(12) United States Patent
Appenzeller et al.

(10) Patent No.: US 8,114,141 B2
(45) Date of Patent: Feb. 14, 2012

(54) DYNAMIC BONE FIXATION ELEMENT AND METHOD OF USING THE SAME

(75) Inventors: Andreas Appenzeller, Biel (CH); Robert Frigg, Bettlach (CH); Beat Lechmann, Grenchen (CH); Cyril Voisard, Niederbipp (CH); Silas Zurschmiede, Grenchen (CH); Urs Hulliger, Deitingen (CH)

(73) Assignee: Synthes USA, LLC, West Chester, PA (US)

( * ) Notice: Subject to any disclaimer, the term of this patent is extended or adjusted under 35 U.S.C. 154(b) by 667 days.

(21) Appl. No.: 12/332,756

(22) Filed: Dec. 11, 2008

(65) Prior Publication Data
US 2009/0157123 A1 Jun. 18, 2009

Related U.S. Application Data

(60) Provisional application No. 61/014,308, filed on Dec. 17, 2007, provisional application No. 61/041,824, filed on Apr. 2, 2008, provisional application No. 61/075,396, filed on Jun. 25, 2008.

(51) Int. Cl.
*A61B 17/04* (2006.01)
*A61B 17/84* (2006.01)
*A61F 2/08* (2006.01)

(52) U.S. Cl. .................... 606/328; 606/306; 606/321

(58) Field of Classification Search .......... 606/306–308, 606/310, 328
See application file for complete search history.

(56) References Cited

U.S. PATENT DOCUMENTS

| | | | |
|---|---|---|---|
| 36,014 A | 7/1862 | Meissner |
| 240,780 A | 4/1881 | Smith |
| 240,913 A | 5/1881 | Lupton |
| 370,136 A | 9/1887 | Goddu |
| 534,164 A | 2/1895 | Larsh |
| 890,447 A | 6/1908 | Perry |
| 1,231,643 A | 7/1917 | Parnall |
| 1,462,126 A | 7/1923 | Ross |
| 1,469,126 A | 9/1923 | Thomas |

(Continued)

FOREIGN PATENT DOCUMENTS
CA 2 560 898 3/2004
(Continued)

OTHER PUBLICATIONS

Michael Bottlang, et al., "Far Cortical Locking Can Reduce Stiffness of Locked Plating Constructs While Retaining Construct Strength", JB& JS: 2009;91:1985-94.

(Continued)

*Primary Examiner* — Thomas C. Barrett
*Assistant Examiner* — Andrew Yang
(74) *Attorney, Agent, or Firm* — Woodcock Washburn LLP

(57) ABSTRACT

The present invention relates to dynamic bone fixation elements and a surgical method to stabilize bone or bone fragments. The dynamic bone fixation elements preferably include a bone engaging component and a load carrier engaging component. The bone engaging component preferably includes a plurality of threads for engaging a patient's bone and a lumen. The load carrier engaging component preferably includes a head portion for engaging a load carrier (e.g., bone plate) and a shaft portion. The shaft portion preferably at least partially extends into the lumen. Preferably at least a portion of an outer surface of the shaft portion is spaced away from at least a portion of an inner surface of the lumen via a gap so that the head portion can move with respect to the bone engaging component. The distal end of the shaft portion is preferably coupled to the lumen.

16 Claims, 18 Drawing Sheets

U.S. PATENT DOCUMENTS

| | | |
|---|---|---|
| 1,756,973 A | 5/1930 | Conner |
| 1,828,287 A | 10/1931 | MacBean |
| 1,828,402 A | 10/1931 | Geyer |
| 1,983,962 A | 12/1934 | Barber et al. |
| 2,045,757 A | 6/1936 | Constantin |
| 2,567,372 A | 9/1951 | Gelpcke |
| 2,586,556 A | 2/1952 | Mullikin |
| 2,672,070 A | 3/1954 | Forster |
| 2,888,853 A | 6/1959 | Pachmayr |
| 3,077,809 A | 2/1963 | Harding et al. |
| 3,298,273 A | 1/1967 | McKelvey |
| 3,350,811 A | 11/1967 | Bender |
| 3,455,360 A | 7/1969 | Simons |
| 3,466,966 A | 9/1969 | Brown |
| 3,495,494 A | 2/1970 | Scott |
| 3,942,329 A | 3/1976 | Babcock |
| 3,945,070 A | 3/1976 | Hauser |
| 4,269,248 A | 5/1981 | MacLean et al. |
| 4,348,141 A | 9/1982 | Dahl |
| 4,395,924 A | 8/1983 | Callahan |
| 4,402,160 A | 9/1983 | Brusasco |
| 4,432,683 A | 2/1984 | Polos |
| 4,437,286 A | 3/1984 | Maguire |
| 4,589,179 A | 5/1986 | Hulting, Jr. |
| 4,724,628 A | 2/1988 | Schreiner |
| 4,756,654 A | 7/1988 | Clough |
| 4,854,797 A | 8/1989 | Gourd |
| 4,906,154 A | 3/1990 | Sheppard |
| 4,947,502 A | 8/1990 | Engelhardt |
| 4,959,064 A | 9/1990 | Engelhardt |
| 4,974,986 A | 12/1990 | Cook |
| 5,061,137 A | 10/1991 | Gourd |
| 5,074,865 A | 12/1991 | Fahmy |
| 5,092,727 A | 3/1992 | Moghe |
| 5,102,276 A | 4/1992 | Gourd |
| 5,351,806 A | 10/1994 | Ohtsuji et al. |
| 5,501,541 A | 3/1996 | Gomes |
| 5,676,356 A | 10/1997 | Ekonen et al. |
| 5,797,234 A | 8/1998 | Theodorou |
| 6,083,224 A | 7/2000 | Gertzbein et al. |
| 6,158,937 A | 12/2000 | Okun |
| 6,368,326 B1 | 4/2002 | Dakin et al. |
| 6,475,242 B1 | 11/2002 | Bramlet |
| 6,508,841 B2 | 1/2003 | Martin et al. |
| 6,524,316 B1 | 2/2003 | Nicholson et al. |
| 6,527,774 B2 | 3/2003 | Lieberman |
| 6,551,320 B2 | 4/2003 | Lieberman |
| 6,554,526 B1 | 4/2003 | Egelandsdal |
| 6,592,292 B2 | 7/2003 | Jansson |
| 6,656,184 B1 | 12/2003 | White et al. |
| 6,908,275 B2 | 6/2005 | Nelson et al. |
| 6,955,513 B2 | 10/2005 | Niku |
| 7,153,326 B1 | 12/2006 | Metzger |
| 7,175,626 B2 | 2/2007 | Neff |
| 7,249,923 B2 | 7/2007 | Niku |
| 2002/0007508 A1 | 1/2002 | Grepper et al. |
| 2002/0198527 A1 | 12/2002 | Muckter |
| 2003/0180117 A1 | 9/2003 | Niku |
| 2003/0202861 A1 | 10/2003 | Nelson et al. |
| 2004/0202526 A1 | 10/2004 | Bunch, Jr. |
| 2005/0010215 A1 | 1/2005 | Delecrin et al. |
| 2005/0143823 A1 | 6/2005 | Boyd et al. |
| 2005/0154390 A1 | 7/2005 | Biedermann et al. |
| 2005/0177167 A1 | 8/2005 | Muckter |
| 2005/0277940 A1 | 12/2005 | Neff |
| 2006/0074421 A1 | 4/2006 | Bickley et al. |
| 2006/0195099 A1 | 8/2006 | Bottlang |
| 2006/0229615 A1 | 10/2006 | Abdou |
| 2006/0264954 A1 | 11/2006 | Sweeney, II et al. |
| 2007/0038219 A1 | 2/2007 | Matthis et al. |
| 2007/0167948 A1 | 7/2007 | Abdou |
| 2007/0191958 A1 | 8/2007 | Abdou |
| 2007/0233062 A1 | 10/2007 | Berry |
| 2007/0282342 A1 | 12/2007 | Niederberger et al. |
| 2008/0021465 A1 | 1/2008 | Shadduck et al. |
| 2008/0071273 A1 | 3/2008 | Hawkes et al. |
| 2008/0188899 A1 | 8/2008 | Bottlang et al. |
| 2009/0018587 A1 | 1/2009 | Bottlang |

FOREIGN PATENT DOCUMENTS

| | | |
|---|---|---|
| CH | 379230 | 9/1961 |
| DE | 1 872 944 | 5/1963 |
| DE | 93 00 056 | 1/1993 |
| DE | 19741087 | 4/1999 |
| DE | 29915204 | 8/1999 |
| DE | 10107201 | 9/2002 |
| DE | 10 2004 006 746 | 5/2005 |
| EP | 0820731 | 1/1998 |
| EP | 1273269 | 1/2003 |
| FR | 736.058 | 9/1932 |
| FR | 958.192 | 3/1950 |
| FR | 2634371 | 1/1990 |
| FR | 2784019 | 4/2000 |
| FR | 2915082 | 10/2008 |
| GB | 572218 | 1/1944 |
| GB | 1051351 | 12/1966 |
| GB | 1067304 | 5/1967 |
| SU | 512315 | 9/1974 |
| SU | 838124 | 9/1979 |
| SU | 838125 | 9/1979 |
| WO | WO 95/02373 | 1/1995 |
| WO | WO 0224087 | 3/2002 |
| WO | WO 2005/044117 | 5/2005 |
| WO | WO 2005/092226 | 10/2005 |
| WO | WO 2006/089292 | 8/2006 |
| WO | WO 2007/049097 | 5/2007 |
| WO | WO 2007/095333 | 8/2007 |
| WO | WO 2007/115016 | 10/2007 |
| WO | WO 2008/034130 | 3/2008 |
| WO | WO 2008/097403 | 8/2008 |

OTHER PUBLICATIONS

Lauterburg, Martin Th., et al., "Forces Involved in Lower Limb Lengthening: An In Vivo Biomechanical Study"., Journal of Orthopaedic Research, Sep. 2006.

Steen, Harald, et al., "Limb Lengthening by Diaphyseal Corticotomy, Callus Distraction, and Dynamic Axial Fixation. An Experimental Study in the Ovine Femur"., Journal of Orthopaedic Research 6:730-735, 1998.

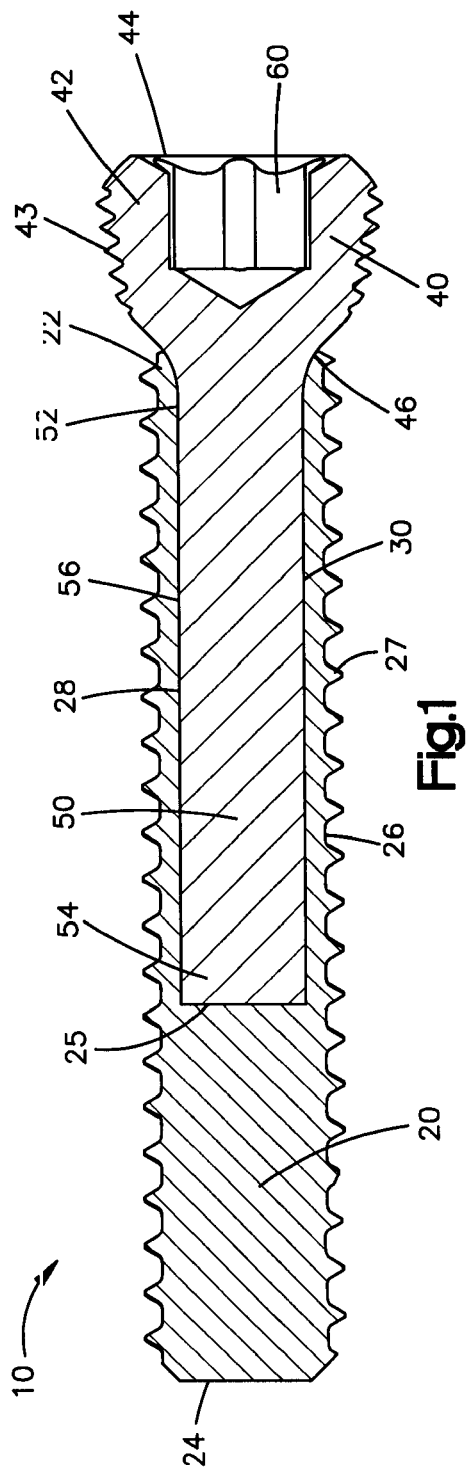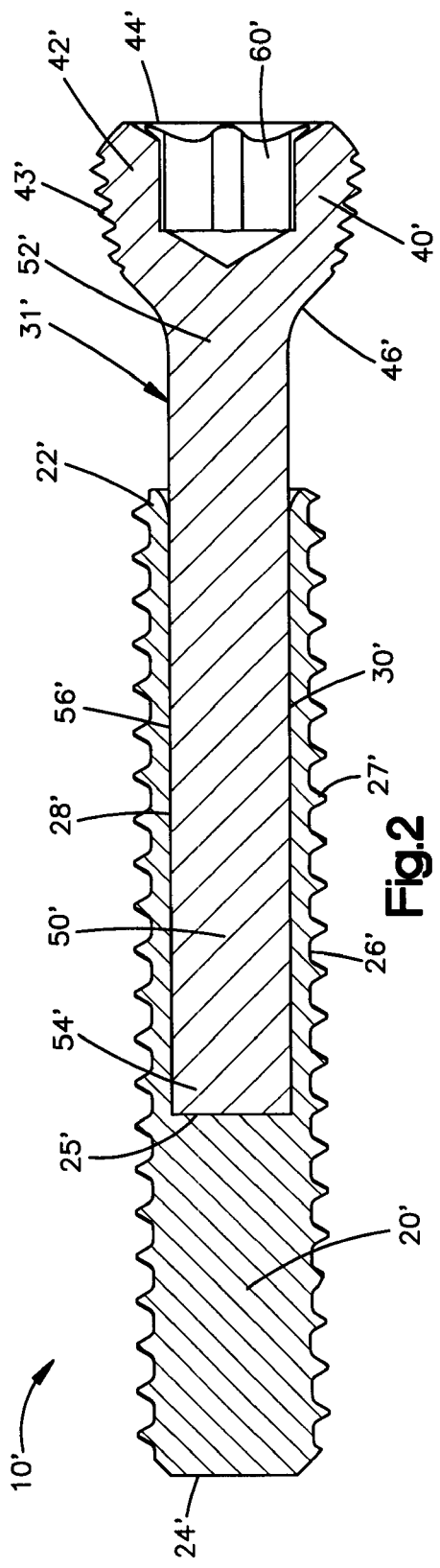

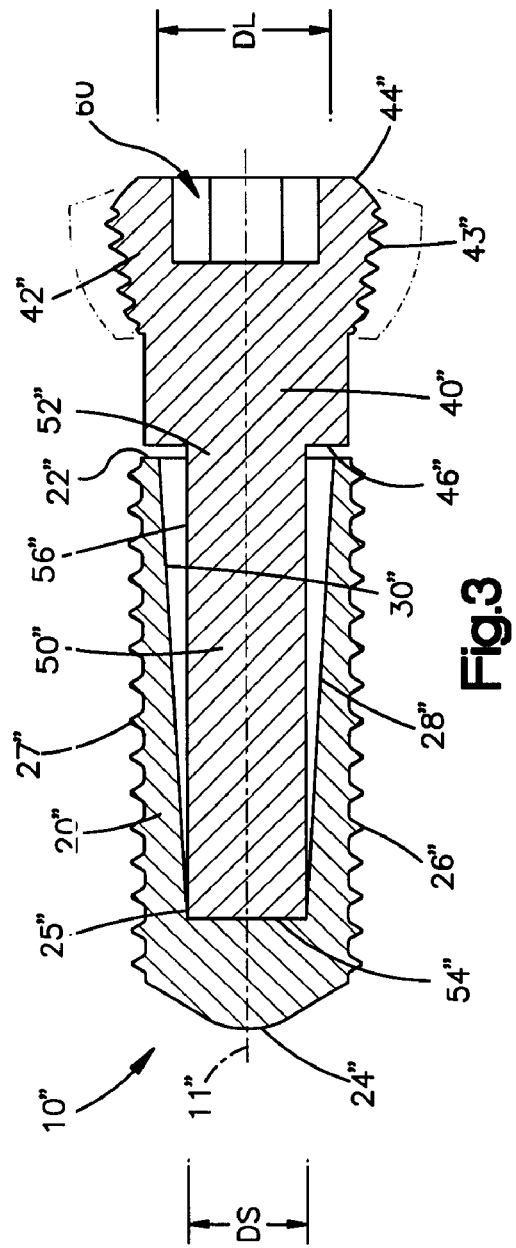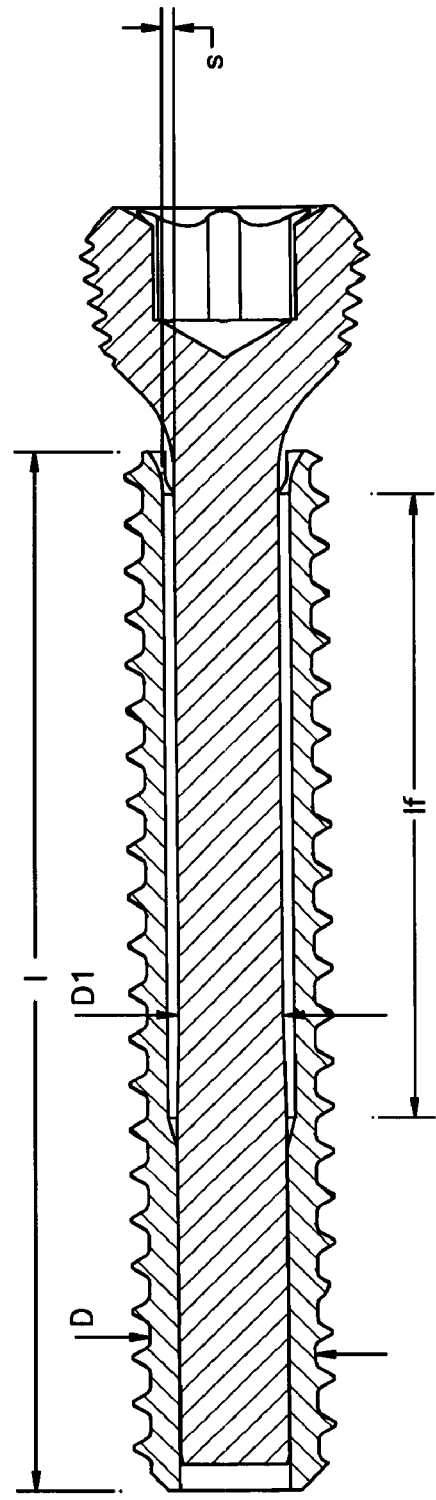
Fig.3
Fig.3A

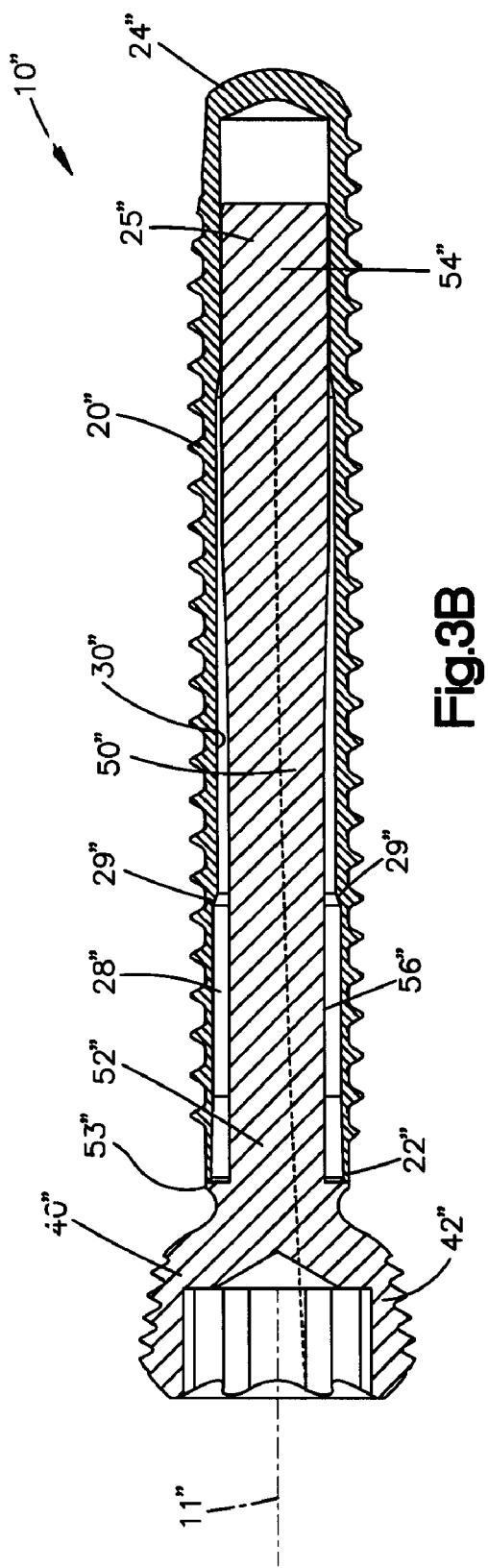
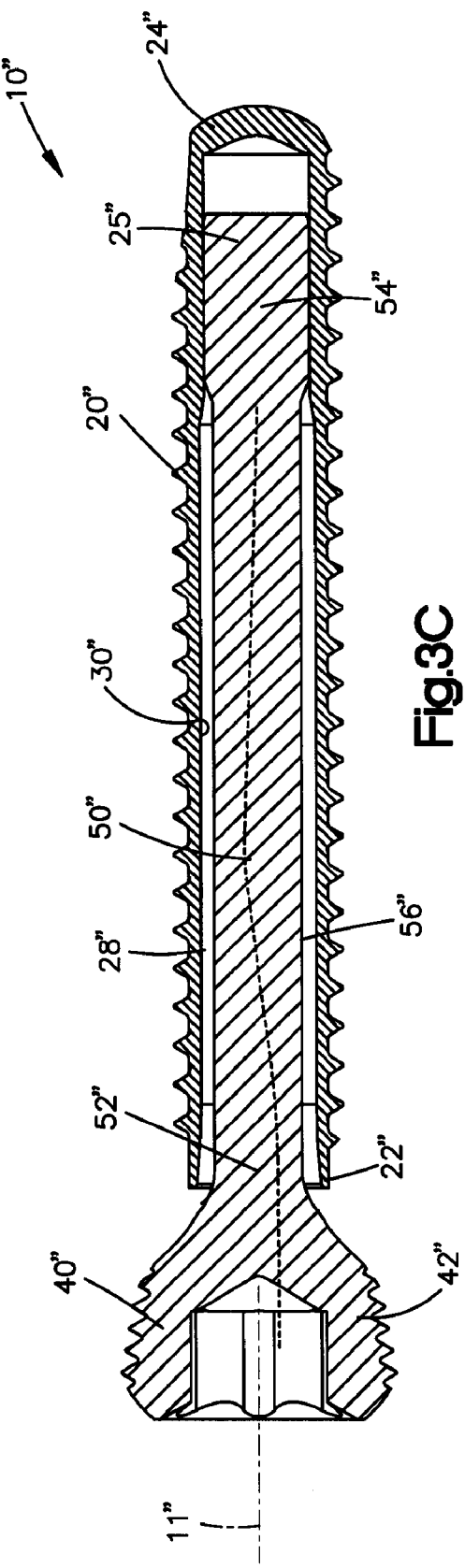
Fig.3B
Fig.3C

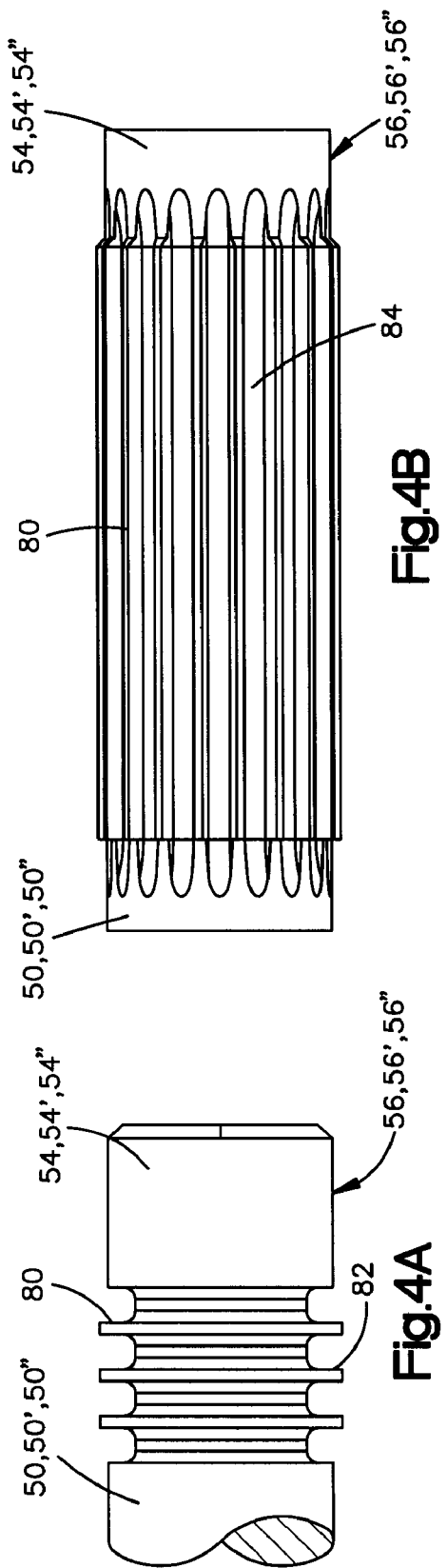
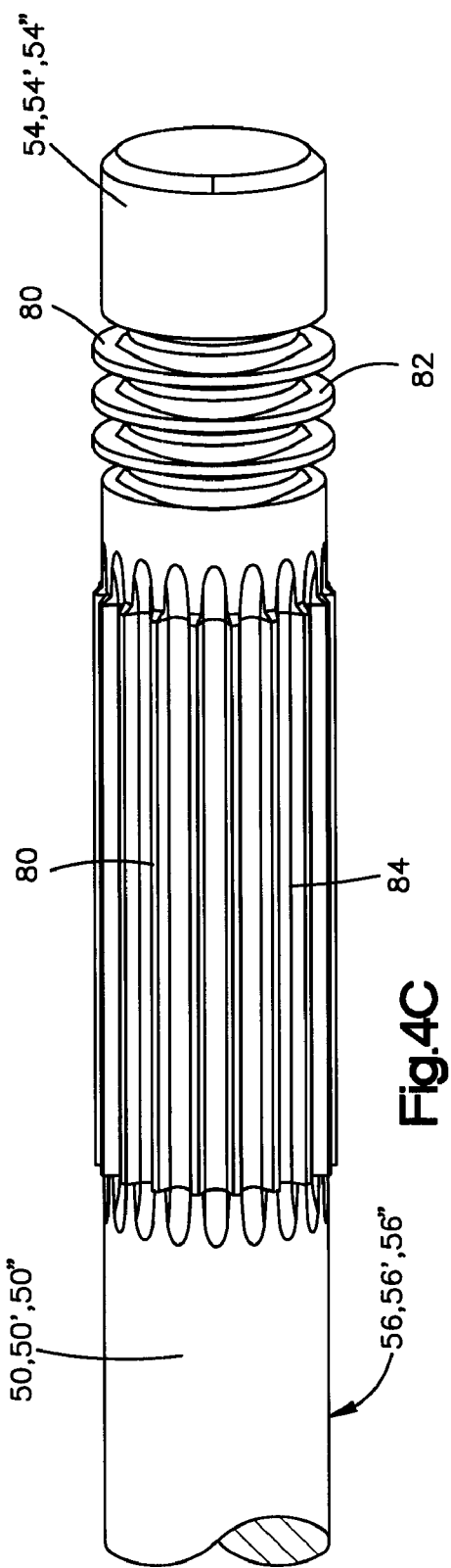
Fig.4A Fig.4B Fig.4C

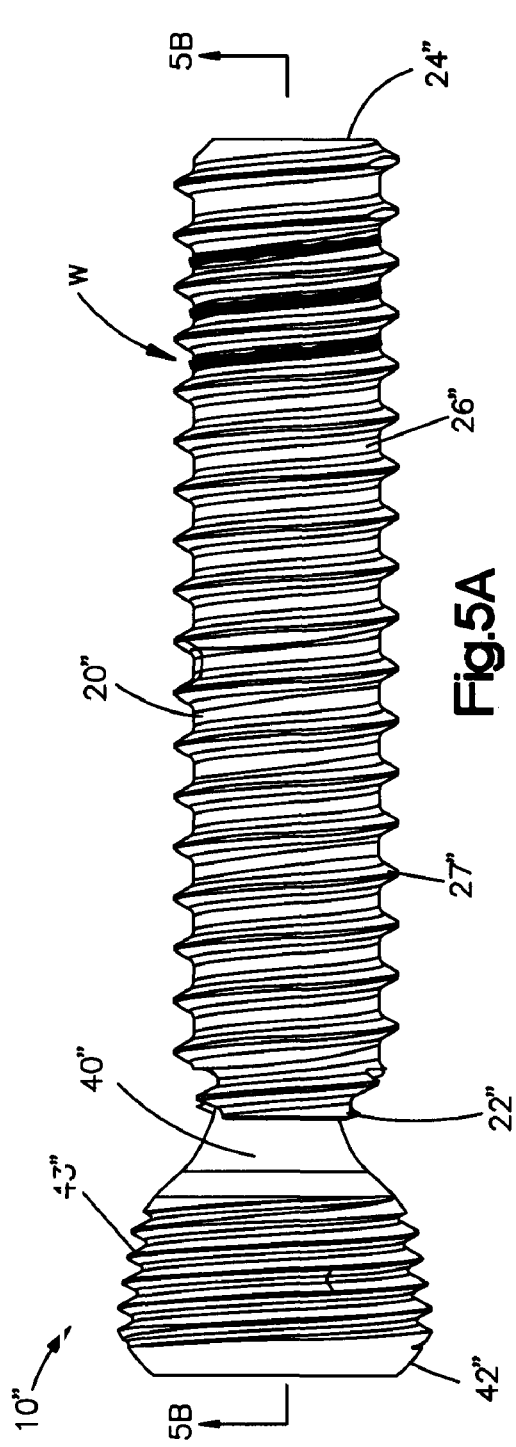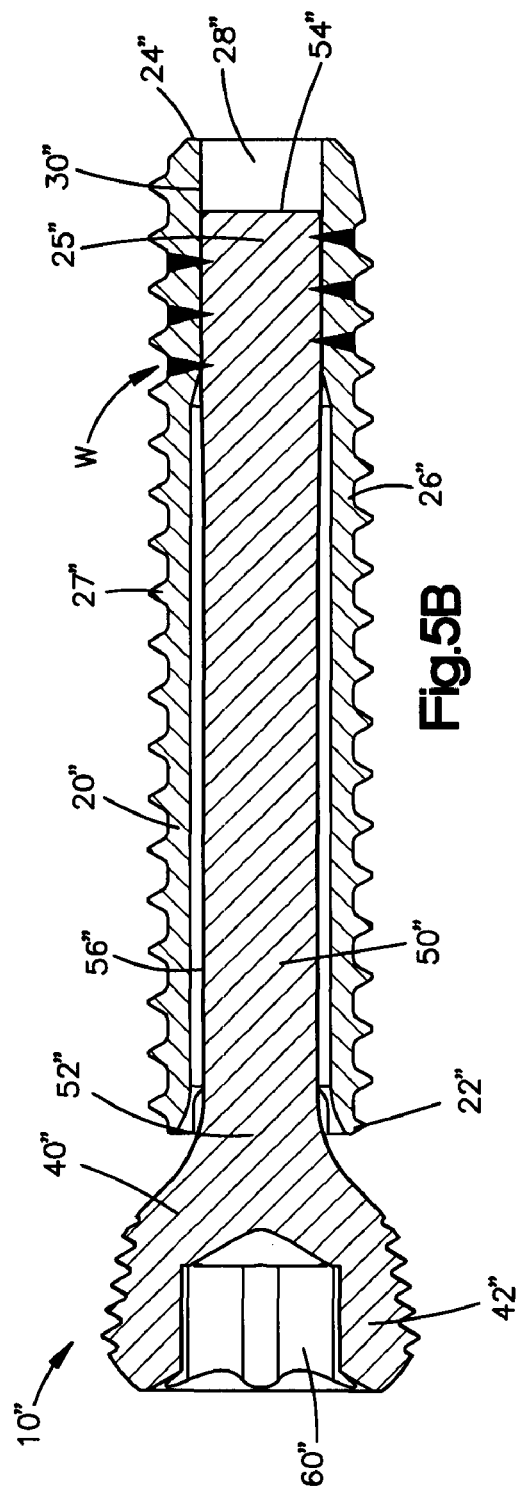

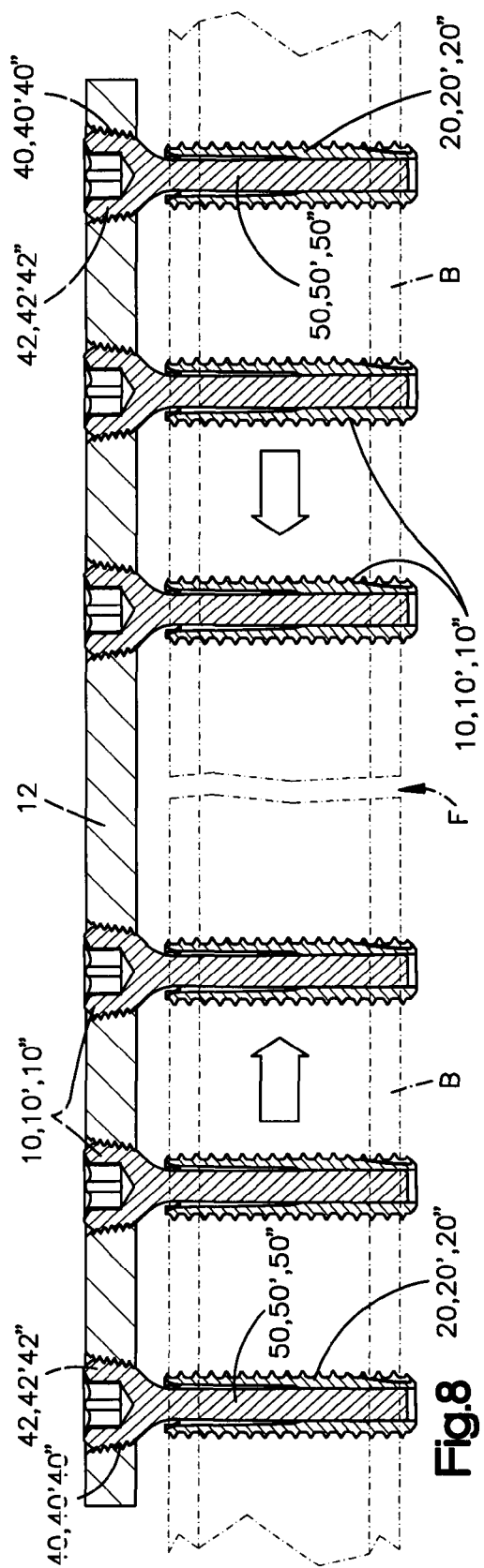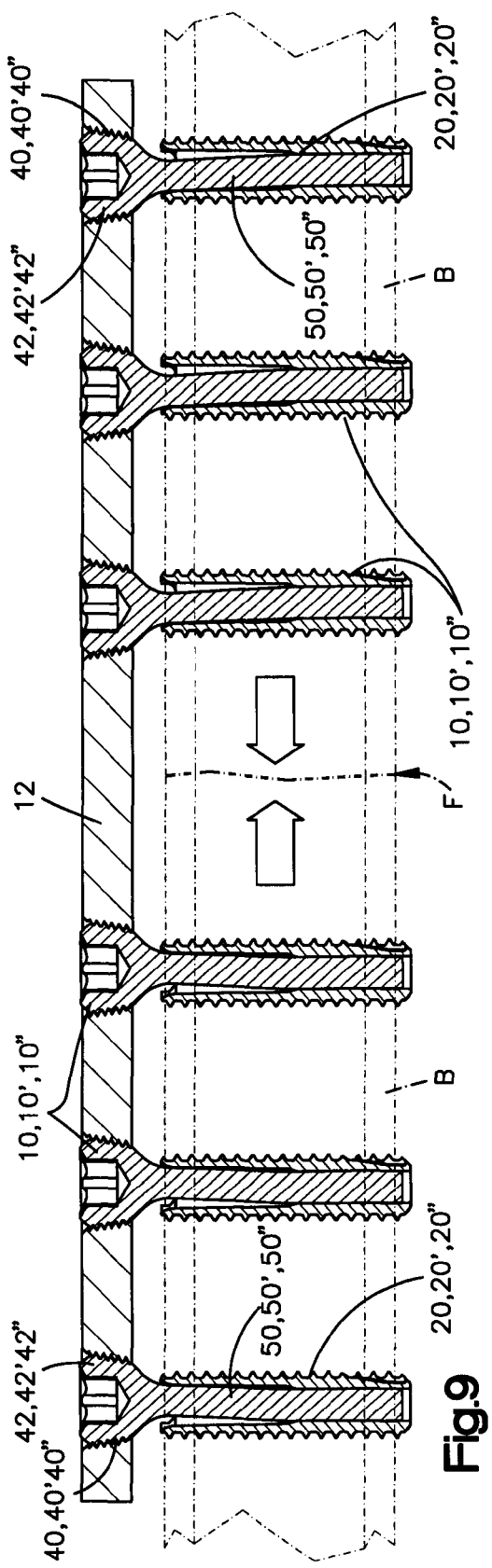

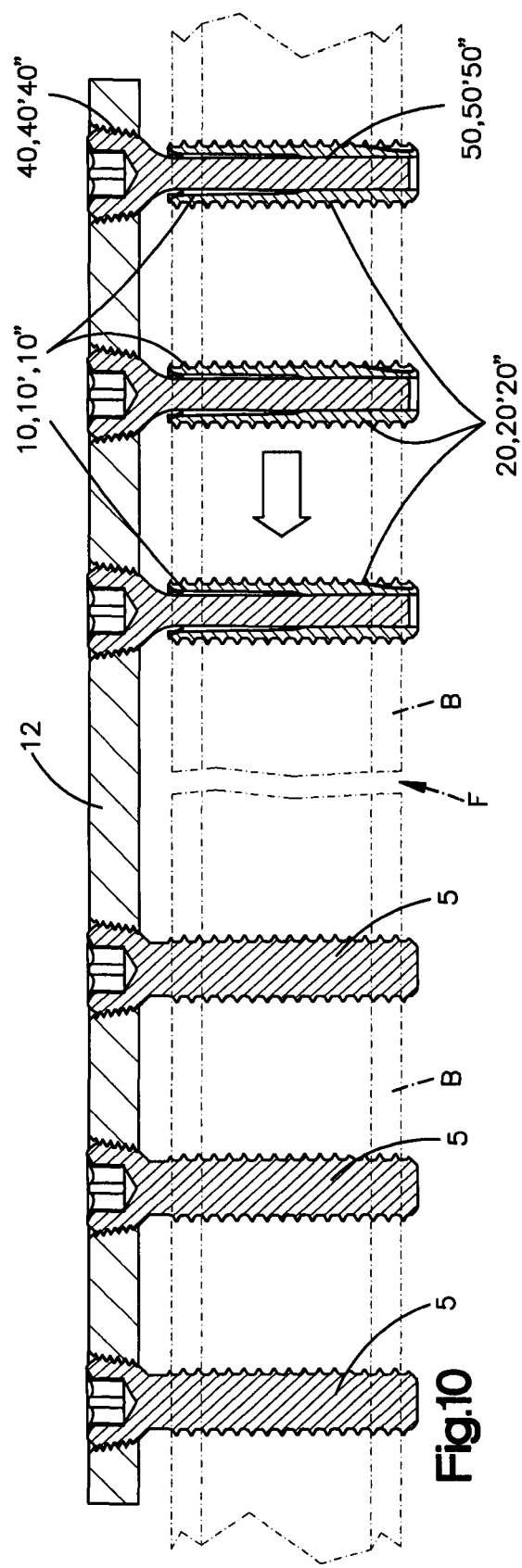

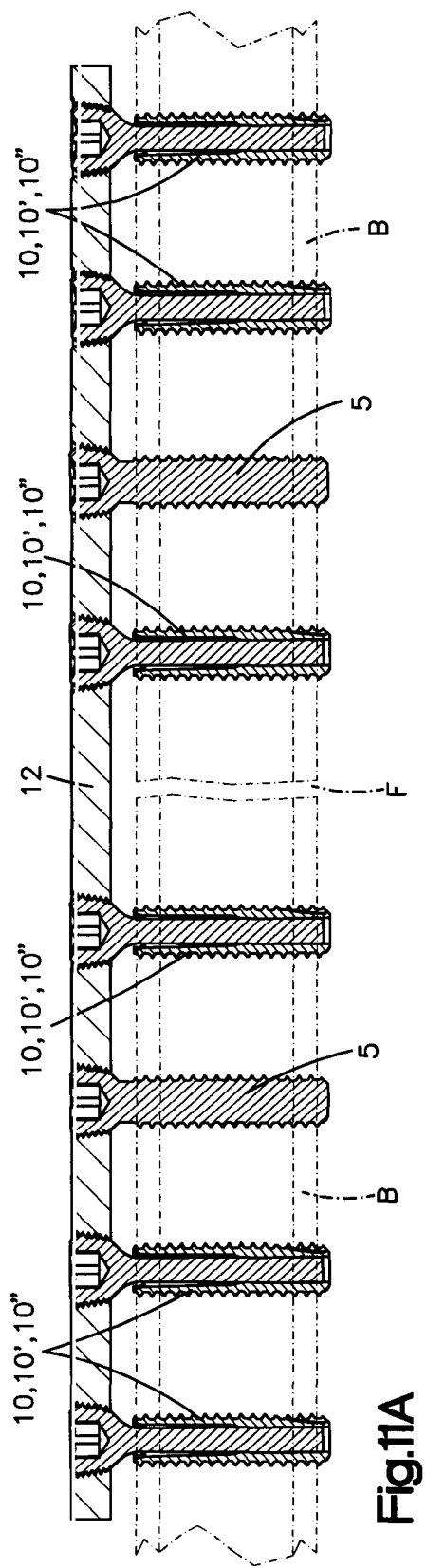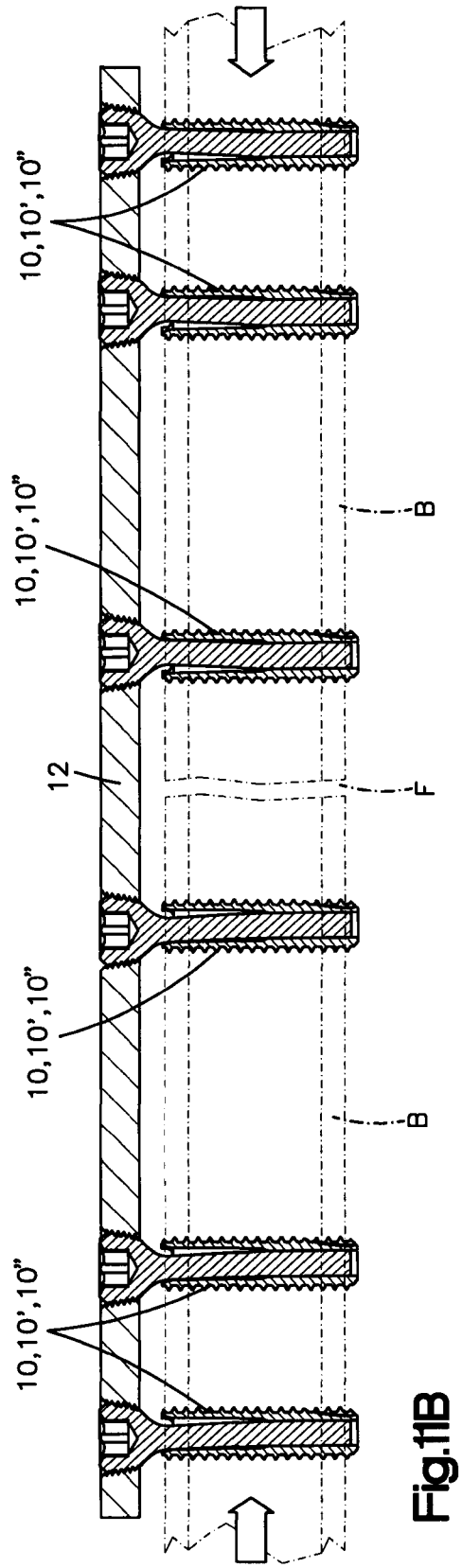

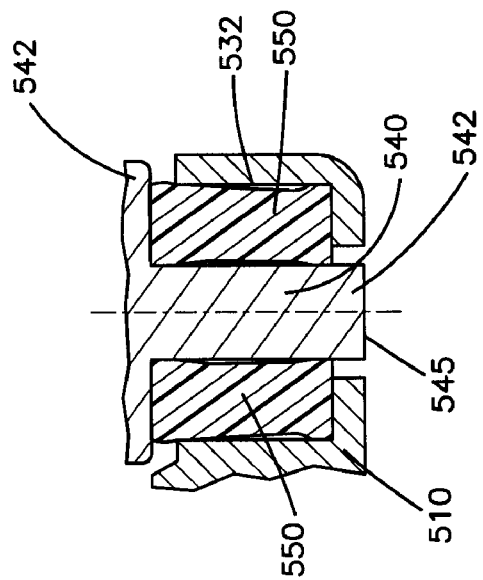
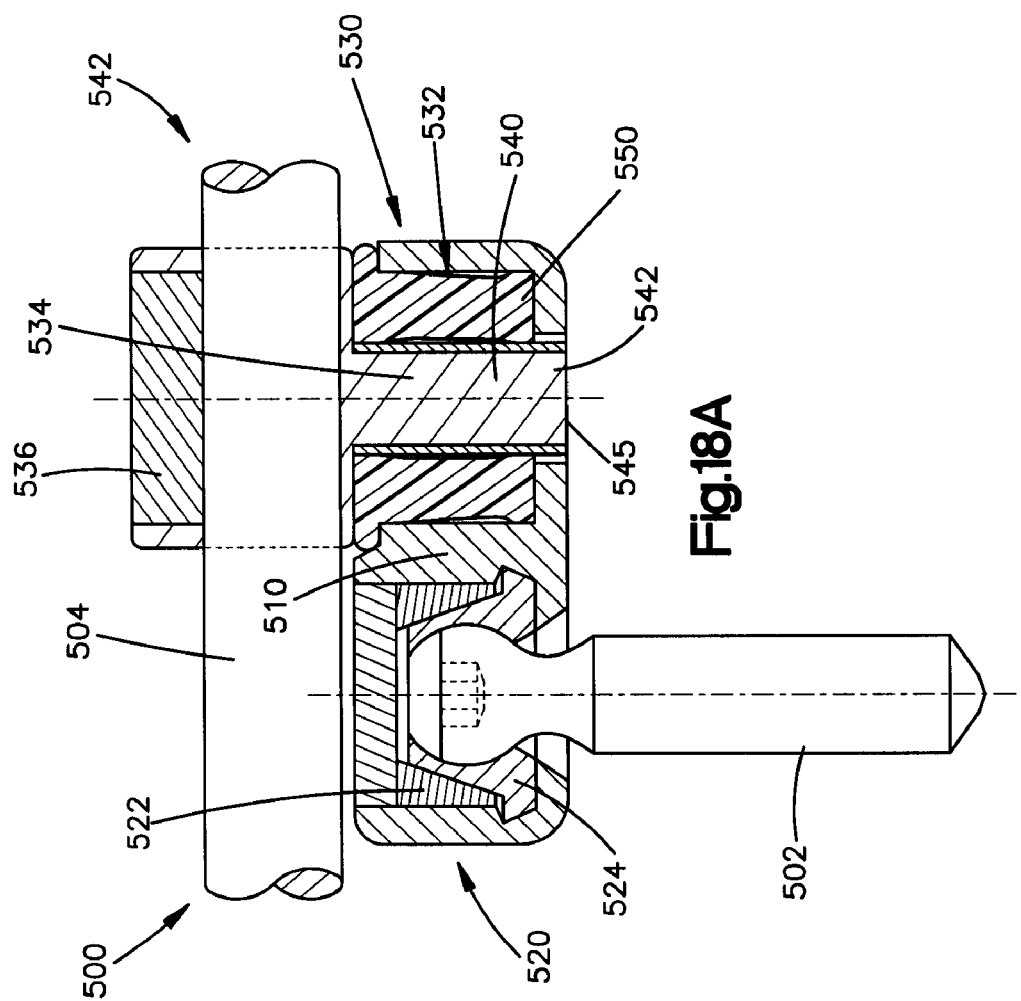

DYNAMIC BONE FIXATION ELEMENT AND METHOD OF USING THE SAME

CROSS REFERENCE TO RELATED APPLICATIONS

This application claims priority to U.S. Provisional Patent Application Ser. No. 61/014,308, filed Dec. 17, 2007, entitled "Dynamic Fixation System"; U.S. Provisional Patent Application Ser. No. 61/041,824, filed Apr. 2, 2008, entitled "Dynamic Fixation System"; and U.S. Provisional Patent Application Ser. No. 61/075,396, filed Jun. 25, 2008, entitled "Stress Controlled Bone Fixation"; the content of which are hereby incorporated by reference in their entirety.

BACKGROUND OF THE INVENTION

Millions of people suffer from bone fractures each year. Treatment of this condition is frequently accomplished by rigid fixation which involves the use of implants such as, for example, longitudinal load carriers (e.g., bone plates, rods, etc.) fixed to a patient's bone or bone fragments via a plurality of bone fixation elements (e.g., bone screws, hooks, pins, rivets, etc.) in order to stabilize the fractured bone across the fracture.

The use of flexible or dynamic fixation in bone fixation is believed to provide advantages by reducing the amount of stress generally associated with rigid fixation, and thus better protect the patient's bone or bone fragments.

SUMMARY OF THE INVENTION

The present invention relates generally to surgical devices and methods to stabilize bones or bone fragments. More specifically, the present invention relates to a dynamic bone fixation element, and a surgical method/procedure to stabilize a bone or bone fragments using the same.

In one exemplary embodiment of the present invention, the dynamic bone fixation element preferably includes a bone engaging component and a load carrier engaging component. The bone engaging component preferably includes a proximal end, a distal end, and a lumen extending at least partially from the proximal end of the bone engaging component. The lumen defines an inner surface. The load carrier engaging component preferably includes a head portion for engaging a load carrier and a shaft portion extending from the head portion. The shaft portion preferably includes a proximal end, a distal end and an outer surface. The shaft portion is preferably sized and configured to at least partially extend into the lumen formed in the bone engaging component. Preferably at least a portion of the shaft portion has a diameter $D_S$ and at least a portion of the lumen has a diameter $D_L$, the diameter $D_L$ being greater than the diameter $D_S$ so that at least a portion of the outer surface of the shaft portion is spaced away from at least a portion of the inner surface of the lumen. In addition, preferably, the distal end of the shaft portion is coupled to the lumen at a position distally of the proximal end of the bone engaging component so that the head portion moves with respect to the bone engaging component and hence the engaged bone or bone fragments may move with respect to the load carrier to enable micro-movement.

The inner surface of the lumen may be tapered at an angle θ such that the diameter $D_L$ of the lumen at a proximal end thereof is larger than the diameter $D_L$ of the lumen at a position distally of the proximal end. The taper angle θ of the lumen is preferably between about zero degrees to about ten degrees.

The shaft portion is preferably integrally formed with the head portion. The shaft portion is preferably coupled to the bone engaging component within the lumen at a position proximate to the distal end of the bone engaging component. The shaft portion is preferably coupled to the bone engaging component within the lumen via a press fit connection. The distal end of the shaft portion preferably has a diameter greater than the diameter $D_L$ of the lumen.

Alternatively and/or in addition, the shaft portion may include one or more textured surfaces formed thereon. The textured surfaces are preferably elastically deformable so that the textured surfaces deform as the shaft portion is being inserted into the lumen. Thereafter the textured surfaces preferably return to their larger original size so that the textured surface press against the inner surface of the lumen to increase a contact pressure between the outer surface of the shaft portion and the inner surface of the lumen. The textured surface may be in the form of a plurality of radially extending ridges formed on a portion of the shaft portion. Alternatively and/or in addition, the textured surface may be in the form of a plurality of longitudinal extending ridges formed on a portion of the shaft portion.

Alternatively and/or in addition, the outer surface of the bone engaging component preferably includes a plurality of threads formed on the outer surface thereof for engaging the patient's bone or bone fragments, the outer surface of the shaft portion may be welded to the inner surface of the lumen by welding in-between adjacent threads formed on the outer surface of the bone engaging component.

The head portion preferably includes a driving element for engaging a tip formed on a drive tool. For example, the head portion may include a plurality of through holes for receiving a plurality of pins formed on the tip of the drive tool, the pins being sized and configured to extend through the head portion of the load carrier engaging component and into contact with the bone engaging component so that the plurality of pins contact both the load carrier engaging component and the bone engaging component such that rotation of the drive tool simultaneously rotates both the load carrier engaging component and the bone engaging component. Alternatively, for example, the head portion may include one or more projections extending therefrom and the bone engaging component includes one or more recesses formed therein so that the projection extends into the recess so that rotation of the drive tool simultaneously rotates both the load carrier engaging component and the bone engaging component.

In another exemplary embodiment, the present invention is directed to a method for internally fixing a load carrier across a fracture in a bone. The method includes the steps of (a) providing a plurality of dynamic bone fixation elements; (b) making an incision; and (c) coupling the load carrier to the patient's bone via two or more dynamic bone fixation elements on either side of the fracture so that the dynamic bone fixation elements enable parallel movement of the bone or bone fragments across the fracture; and (d) closing the incision so that the load carrier and plurality of dynamic bone fixation elements remain within the patient. Preferably the dynamic bone fixation elements each include a bone engaging component for engaging the bone and a load carrier engaging component for engaging the load carrier, the bone engaging component being movably associated with the load carrier engaging component so that movement of the load carrier engaging component with respect to the bone engaging component enables the parallel movement of the bone or bone fragments across the fracture. The bone engaging component preferably includes a lumen extending at least partially from a proximal end of the bone engaging component, the lumen defining an inner surface. The load carrier engaging component preferably includes a head portion for engaging the load carrier and a shaft portion extending from the head portion, the shaft portion having a proximal end, a distal end and an outer surface, the shaft portion being sized and configured to at least partially extend into the lumen formed in the bone engaging component. Preferably, at least a portion of the outer surface of the shaft portion is spaced away from at least a portion of the inner surface of the lumen so that the head portion moves with respect to the bone engaging component.

The method for fixing the load carrier across the fracture in the bone may also include inserting one or more standard bone screws on one or both sides of the fracture F so that micro-movement of the bone is prevented for an initial period of time so that thereafter the standard bone screws may be removed from the patient's bone after the initial period of time has lapsed so that micro-movement of the bone is enabled.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred dynamic bone fixation elements and surgical procedure and/or method of the present application, there is shown in the drawings preferred embodiments. It should be understood, however, that the application is not limited to the precise arrangements and instrumentalities shown. In the drawings:

FIG. 1 shows a cross-sectional view of a dynamic bone fixation element according to a first exemplary embodiment of the present invention;

FIG. 2 shows a cross-sectional view of a dynamic bone fixation element according to a second exemplary embodiment of the present invention;

FIG. 3 shows a cross-sectional view of a dynamic bone fixation element according to a third exemplary embodiment of the present invention;

FIG. 3A shows a cross-sectional view of an alternate embodiment of the dynamic bone fixation element shown in FIG. 3, the cross-sectional view illustrating preferred, exemplary dimensions of the dynamic bone fixation element;

FIG. 3B shows a cross-sectional view of an alternate embodiment of the dynamic bone fixation element shown in FIG. 3, the cross-sectional view illustrating an exemplary dynamic bone fixation element for use in spinal procedures;

FIG. 3C shows a cross-sectional view of an alternate embodiment of the dynamic bone fixation element shown in FIG. 3, the cross-sectional view illustrating an exemplary dynamic bone fixation element for use in trauma procedures;

FIG. 4A shows a detailed view of a plurality of radially extending ridges or lamellas formed on a distal end of a shaft portion of a load carrier engaging component in accordance with one exemplary embodiment of the load carrier engaging component;

FIG. 4B shows a detailed view of a plurality of longitudinally extending ridges or lamellas formed on a distal end of a shaft portion of a load carrier engaging component in accordance with one exemplary embodiment of the load carrier engaging component;

FIG. 4C shows a detailed view of a plurality of radially extending ridges or lamellas and a plurality of longitudinally extending ridges or lamellas formed on a distal end of a shaft portion of a load carrier engaging component in accordance with one exemplary embodiment of the load carrier engaging component;

FIG. 5A shows a side view of an exemplary method for coupling a shaft portion of a load carrier engaging component to a bone engaging component in accordance with one exemplary embodiment of the present invention;

FIG. 5B shows a cross sectional view of the exemplary method for coupling the shaft portion of the load carrier engaging component to the bone engaging component taken along line 5B-5B shown in FIG. 5A;

FIG. 8 shows a cross-sectional view of an exemplary method for long bone fixation in accordance with a first exemplary surgical method of the present invention;

FIG. 9 shows a second cross-sectional view of the exemplary method for long bone fixation shown in FIG. 8;

FIG. 10 shows a cross-sectional view of an exemplary method for long bone fixation in accordance with a second exemplary surgical method of the present invention;

FIG. 11A shows a cross-sectional view of an exemplary method for long bone fixation in accordance with a third exemplary surgical method of the present invention;

FIG. 11B shows a second cross-sectional view of the exemplary method for long bone fixation shown in FIG. 11A;

FIG. 18A shows a cross-sectional view of a dynamic pedicle screw fixation clamp according to a first exemplary embodiment of the present invention;

FIG. 18B shows a detailed, cross-sectional view of a portion of the dynamic pedicle screw fixation clamp shown in FIG. 18A;

DETAILED DESCRIPTION OF THE INVENTION

Figure 6A:
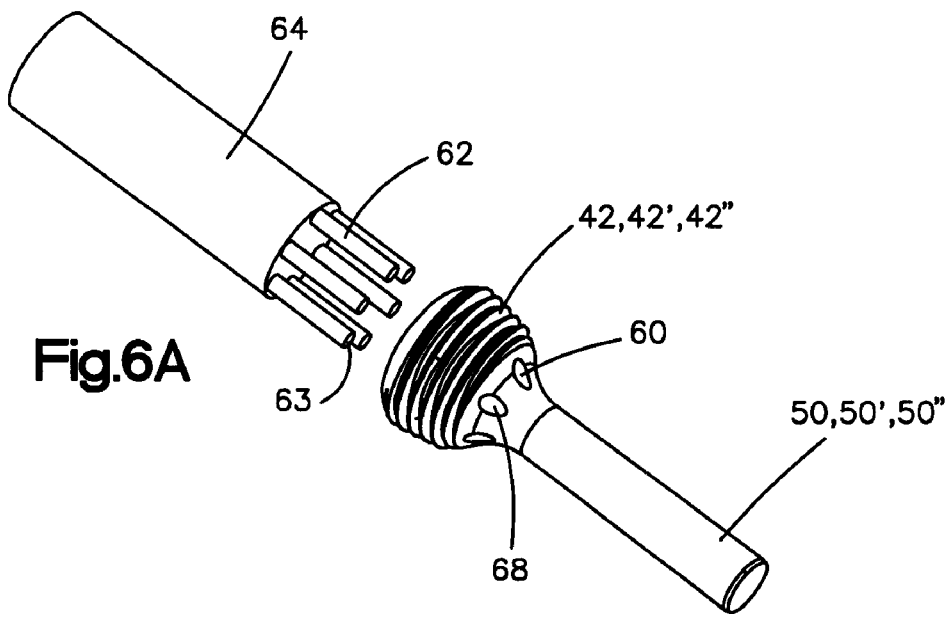
FIG. 6A shows an exploded, perspective view of a drive element for coupling a head portion of a dynamic bone fixation element to a drive tool in accordance with a first preferred embodiment of the present invention.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, the present invention relates to a dynamic bone fixation element 10, 10', 10", and a surgical procedure and/or method for the flexible or dynamic fixation of a patient's bone or bone fragments B. More specifically, the present invention relates to various embodiments of a dynamic bone fixation element 10, 10', 10", and a surgical procedure and/or method for internal long bone fixation using a plurality of dynamic bone fixation elements 10, 10', 10" to stabilize a patient's bone B across a fracture site F. As generally understood by one of ordinary skill in the art, it should be understood that while the dynamic bone fixation elements 10, 10', 10", and surgical procedure and/or method for internal long bone fixation will be described in connection with a patient's long bone B such as, for example, a femur (thigh), tibia and fibula (leg), humerus (upper arm), radius and ulna (lower arm), etc., those skilled in the art will appreciate that the dynamic bone fixation elements 10, 10', 10", and surgical procedure and/or method for long bone fixation may be used in other surgical procedures such as, for example, in spinal surgeries, maxillofacial bone fixation, external fixation, etc.

Generally speaking, as will be described in greater detail below, a dynamic bone fixation element 10, 10', 10" preferably includes a first bone engaging component 20, 20', 20" such as, for example, an externally threaded bone screw, a hook, a bolt, a pin, a rivet, etc., and a second longitudinal load carrier engaging component 40, 40', 40" such as, for example, an enlarged head portion 42, 42', 42". The load carrier engaging component 40, 40', 40" is movably associated with the bone engaging component 20, 20', 20" so that in use incorporation of the dynamic bone fixation element 10, 10', 10" enables movement of the load carrier engaging component 40, 40', 40" with respect to the bone engaging component 20, 20', 20" so that the engaged bone B may move with respect to the load carrier 12. That is, as will be described in greater detail below, the load carrier engaging component 40, 40', 40" includes a head portion 42, 42', 42" for engaging, for example, a bone plate 12 or rod, and a shaft portion 50, 50, 50". The bone engaging component 20, 20', 20" includes, for example, a plurality of external threads 27, 27', 27" for engaging a patient's bone B and an inner lumen 28, 28', 28" for receiving at least a portion of the shaft portion 50, 50', 50". The outer surface 56, 56', 56" of the shaft portion 50, 50', 50" and the inner surface 30, 30', 30" of the lumen 28, 28', 28" are preferably sized and configured such that there is a clearance or gap therebetween. In addition, the head portion 42, 42', 42" of the load carrier engaging component 40, 40', 40" is not directly coupled to the bone engaging component 20, 20', 20" so that, preferably, there is a clearance or gap between the distal end 46, 46', 46" of the head portion 42, 42', 42" and the proximal end 22, 22', 22" of the bone engaging component 20, 20', 20". Therein, insertion of the shaft portion 50, 50', 50" of the load carrier engaging component 40, 40', 40" into the lumen 28, 28', 28" formed in the bone engaging component 20, 20', 20" enables the dynamic bone fixation element 10, 10', 10" to flex and/or move in order to enable and/or absorb micro-movement of the bone B with respect to the load carrier 12.

Referring to FIG. 1, the dynamic bone fixation element 10 of a first preferred embodiment preferably includes a first bone engaging component 20 such as, for example, an externally threaded bone screw for engaging a patient's bone B, and a second load carrier engaging component 40 such as, for example, an enlarged head portion 42. The externally threaded bone screw includes an inner lumen 28 for receiving a shaft portion 50 extending from the head portion 42 of the load carrier engaging component 40. That is, the bone engaging component 20 includes a proximal end 22, a distal end 24, an outer surface 26 and a lumen 28. The lumen 28 extends at least partially through the bone engaging component 20 from the proximal end 22 to an end 25 proximal of the distal end 24.

In a preferred embodiment, the outer surface 26 of the bone engaging component 20 includes a plurality of threads 27 extending along a length thereof for engaging the fractured bone or bone fragments B. The angle and the shape of the threads 27 may be varied to meet specific anchoring needs, such as, for example, in osteoporotic bones. The distal end 24 of the bone engaging component 20 may be tapered to include a self-tapping or a self-drilling tip as would be understood by those skilled in the art.

The load carrier engaging component 40 includes a shaft portion 50 having an outer surface 56, and the head portion 42. The shaft portion 50 extends longitudinally from a proximal end 52 to a distal end 54 and is sized and shaped to at least partially fit within the lumen 28 of the bone engaging component 20. As shown, the head portion 42 may protrude radially outward from the proximal end 52 of the shaft portion 50 with a radius greater than that of the outer surface 56 of the shaft portion 50. The entire shaft portion 50 may be received within the lumen 28 such that the distal end 46 of the head portion 42 abuts the proximal end 22 of the bone engaging component 20.

Alternatively, referring to a second embodiment of the dynamic bone fixation element 10' as best shown in FIG. 2, the lumen 28' formed in the bone engaging component 20' may be shorter than a length of the shaft portion 50' extending from the head portion 42' of the load carrier engaging portion 40' such that only a portion of the shaft portion 50' fits within the lumen 28' while a neck portion 31' protrudes from the bone engaging component 20'. The neck portion 31' may flex permitting the head portion 42' to move relative to the distal portion 54' of the shaft portion 50' and/or relative to the bone engaging component 20'. In use, the neck portion 31' of the dynamic bone fixation element 10' is preferably positioned between a bone facing surface 13 of the load carrier 12 and the patient's bone or bone fragments B such that the neck portion 31' may move and/or deform as necessary to accommodate micro-movement of the patient's bone or bone fragments B.

Preferably, referring to a third preferred embodiment of the dynamic bone fixation element 10" as best shown in FIGS. 3-3C, the shaft portion 50" extending from the head portion 42" of the load carrier engaging component 40" has a diameter $D_S$ smaller than a diameter of the lumen $D_L$ formed in the bone engaging component 20" such that a gap (e.g., an annular space) exists between the outer surface 56" of the shaft portion 50" and an inner surface 30" of the lumen 28" so that the head portion 42" can move relative to the bone engaging component 20". Preferably the dynamic bone fixation element 10" allows about two millimeters of movement of the head portion 42" away from a longitudinal axis 11" of the dynamic bone fixation element 10". In other embodiments more or less flexing of the shaft portion 50" and more or less movement of the head portion 42" is possible. The distal end 54" of the shaft portion 50" is preferably coupled and/or attached to the lumen 28" at end 25" such that the shaft portion 50" has greater freedom of movement within the lumen 28", as will be described in greater detail below. It will be understood by those of skill in the art that the size of the gap may be adjusted to adjust the amount of permitted movement between the bone engaging component 20" and the load carrier engaging component 40".

In addition and/or alternatively, the lumen 28" formed in the bone engaging component 20" may be tapered such that a diameter of the lumen 28" at the proximal end 22" of the bone engaging component 20" is larger than a diameter of the lumen 28" at end 25". The taper angle θ of the lumen 28" may be between about zero to about ten degrees. It will be understood by those of skill in the art that the taper angle θ may be adjusted to adjust the amount of permitted movement between the bone engaging component 20" and the load carrier engaging component 40". In use, the size of the taper angle θ may be used to limit the maximum amount of movement between the head portion 42" of the load carrier engaging component 40" and the bone engaging component 20" by limiting how far the shaft portion 50" may flex and/or move before the outer surface 56" of the shaft portion 50" contacts the inner surface 30" of the lumen 28" formed in the bone engaging component 20". It should be noted that the outer surface 56" of the shaft portion 50" may be tapered instead of or in addition to tapering the inner surface 30" of the lumen 28". Alternatively and/or in addition, the distal end 46" of the head portion 42" and the proximal end 22" of the bone engaging component 20" may be angled (angle α) to provide increased clearance between the head portion 42" and the bone engaging component 20".

With particular reference to FIGS. 3B and 3C, to satisfy the different loads anticipated in spine and trauma procedures, generally speaking, for spinal applications (as best shown in FIG. 3B), preferably the distal end 54" of the shaft 50" has a larger diameter than the proximal end 52" of the shaft 50" to accommodate the higher anticipated stresses that the distal end 54" of the shaft 50" is expected to experience. Thus, for spine specific embodiments where straight bending as opposed to S-bending is expected, the outer surface 56" of the shaft 50" is preferably tapered so that the distal end 54" of the shaft 50" has a larger diameter than the proximal end 52" of the shaft 50". In addition, the lumen 28" formed in the bone engaging component 20" preferably includes one or more conically or "stepped" cylindrically shaped surfaces 29" to accommodate the increased motion of the shaft 50" with respect to the bone engaging component 20". As shown, the lumen 28" may also include a "trumpet"-shaped distal end and the shaft 50" may include a conical shape with an ellipsoid neck at the head portion and a lip 53" at the proximal end thereof for contacting the proximal end 22" of the bone engaging component 20".

This is in contrast to trauma applications (as best shown in FIG. 3C) such as, long bone fixation, where it is generally not necessary to increase the diameter of the distal end 54" of the shaft 50" since the shaft 50" generally undergoes S-bending (something it won't do in spine applications) and hence, in trauma applications, the distal and proximal ends 52", 54" of the shaft 50" experience approximately the same amount of force. Thus, preferably trauma-specific embodiments can include a shaft 50" that has a constant diameter for the entire length or most of the length of the shaft 50", which is easier to manufacture than a shaft 50" that gradually increases in diameter or has an increased diameter portion at the distal end 54" thereof. As shown, for trauma specific embodiments where S-bending is expected, the lumen 28" may include a cylindrical shape and a trumpet-shaped distal end while the shaft 50" may include a cylindrical shape and an ellipsoid-shaped neck at the head portion.

The shaft portion 50, 50', 50" may be integrally formed with the head portion 42, 42', 42". Alternatively, the shaft portion 50, 50', 50" may be coupled to the head portion 42, 42', 42" by any means now or hereafter known including but not limited to adhesive, welding, soldering, brazing, press-fit, friction fit, interference fit, a threaded connection, pinning, shrinking, engrailing, a cotter-pin, one or more fasteners such as via a pin or screw inserted longitudinally or radially, etc. In addition, the shaft portion 50, 50', 50" may be any size, shape and configuration including but not limited to straight, tapered, curved, solid, hollow, slotted, or formed as a spring like member such as, for example, a helical spring.

The head portion 42, 42', 42" may also include a plurality of external threads 43, 43', 43" for engaging the load carrier 12 such that the dynamic bone fixation element 10, 10', 10" may be locked to the load carrier 12. It will be understood by those of skill in the art that the load carrier 12 includes a plurality of openings 14 through which the dynamic bone fixation elements 10, 10', 10" are inserted into the bone or bone fragments B and that the openings 14 may be threaded to engage the threading 43, 43', 43" formed on the head portion 42, 42', 42" of the load carrier engaging component 40, 40', 40". The head portion 42, 42', 42" preferably also includes a driving element 60, as will be described in greater detail below. It will also be understood by those of skill in the art that the head portion 42, 42', 42" may take any size and shape so long as the head portion 42, 42', 42" is structured to engage the load carrier 12 in a desired manner.

The shaft portion 50, 50', 50" of the load carrier engaging component 40, 40', 40" may be integrally formed with the bone engaging component 20, 20', 20". Alternatively, the shaft portion 50, 50', 50" of the load carrier engaging component 40, 40', 40" may be coupled to the bone engaging component 20, 20', 20", preferably within the lumen 28, 28', 28", by any means now or hereafter known including but not limited to adhesive, welding, soldering, brazing, press-fit, friction fit, interference fit, a threaded connection, pinning, shrinking, engrailing, a cotter-pin, one or more fasteners such as via a pin or screw inserted longitudinally or radially, etc.

Preferably, the shaft portion 50, 50', 50" of the load carrier engaging component 40, 40', 40" is coupled to the bone engaging component 20, 20', 20" within the lumen 28, 28', 28" formed in the bone engaging component 20, 20', 20". That is, in a preferred embodiment, the shaft portion 50, 50', 50" is inserted into the lumen 28, 28', 28" and attached to the bone engaging component 20, 20', 20" at end 25, 25', 25", located distally of the proximal end 22, 22', 22" of the bone engaging component 20, 20', 20", and more preferably adjacent or proximate to the distal end 24, 24', 24" of the bone engaging component 20, 20', 20". More preferably, the shaft portion 50, 50', 50" of the load carrier engaging component 40, 40', 40" is secured within the lumen 28, 28', 28" formed in the bone engaging component 20, 20', 20" by a press fit. That is, generally speaking, the diameter $D_L$ of the lumen 28, 28', 28" formed in the bone engaging component 20, 20', 20" is slightly smaller than the diameter $D_S$ of at least a portion of the shaft portion 50, 50', 50" (preferably the distal end 54, 54', 54" of the shaft portion 50, 50', 50") so that some amount of force is required to insert and remove the shaft portion 50, 50', 50" from the bone engaging component 20, 20', 20". In this manner, the press fit engagement of the shaft portion 50, 50', 50" with the bone engaging component 20, 20', 20" ensures that the load carrier engaging component 40, 40', 40" will not separate from the bone engaging component 20, 20', 20" and enables transfer of longitudinal and torsional forces between the load carrier engaging component 40, 40', 40" and the bone engaging component 20, 20', 20".

Referring to FIGS. 4A-4C, in order to increase the coupled strength between the load carrier engaging component 40, 40', 40" and the bone engaging component 20, 20', 20", the shaft portion 50, 50', 50" of the load carrier engaging component 40, 40', 40" may include one or more textured surfaces 80 formed thereon. In use, the textured surfaces 80 are sized and configured, either in connection with the diameter $D_S$ of the shaft portion 50, 50', 50" or alone, to be slightly oversized as compared to the diameter $D_L$ of the lumen 28, 28', 28" formed in the bone engaging component 20, 20', 20". During assembly, the textured surfaces 80 deform as the shaft portion 50, 50', 50" is being inserted into the lumen 28, 28', 28" formed in the bone engaging component 20, 20', 20". Thereafter, preferably due to material elasticity, the textured surface 80 returns to its original size thereby causing the textured surface 80 to press against the inner surface 30, 30', 30" of the lumen 28, 28', 28" to increase the resistance against the shaft portion 50, 50', 50" moving and/or separating from the bone engaging component 20, 20', 20". That is, providing textured surfaces 80 on the outer surface 56, 56', 56" of the shaft portion 50, 50', 50" increases the contact pressure between the outer surface 56, 56', 56" of the shaft portion 50, 50', 50" and the inner surface 30, 30', 30" of the lumen 28, 28', 28" and thus increases the transferable forces and the contact strength between the shaft portion 50, 50', 50" and the bone engaging component 20, 20', 20". As best shown in FIG. 4A, the textured surface 80 may be in the form of a plurality of radially extending ridges or lamellas 82 formed on a portion of the shaft portion 50, 50', 50", preferably adjacent to the distal end 54, 54', 54" of the shaft portion 50, 50', 50". Providing radial ridges or lamellas 82 increases the axial or pull out strength of the shaft portion 50, 50', 50" with respect to the bone engaging component 20, 20', 20". Alternatively, as best shown in FIG. 4B, the textured surface 80 may be in the form of a plurality of longitudinal extending ridges or lamellas 84 formed on a portion of the shaft portion 50, 50', 50", preferably adjacent to the distal end 54, 54', 54" of the shaft portion 50, 50', 50". Providing longitudinal ridges or lamellas 84 increases the torque or torsional strength of the shaft portion 50, 50', 50" with respect to the bone engaging component 20, 20', 20". Alternatively, as best shown in FIG. 4C, the shaft portion 50, 50', 50" may include a plurality of radial ridges or lamellas 82 and a plurality of longitudinal ridges or lamellas 84 in order to increase both the axial and torsional strength of the shaft portion 50, 50', 50" with respect to the bone engaging component 20, 20', 20". As will be appreciated by one of ordinary skill in the art the ridges or lamellas 82, 84 may have other shapes including, for example, spiral shaped.

Alternatively and/or in addition, as best shown in FIGS. 5A and 5B, the shaft portion 50, 50', 50" may be inserted into the lumen 28, 28', 28" formed in the bone contacting component 20, 20', 20" and welded W to the bone contacting component 20, 20', 20". The shaft portion 50, 50', 50" may be welded W to the bone contacting component 20, 20', 20" from the outside of the dynamic bone fixation element 10, 10', 10" by spiraling welding W between adjacent threads 27, 27', 27" formed on the outer surface 26, 26', 26" of the bone contacting component 20, 20', 20". By using the threads 27, 27', 27" as a weld path, damage to the thread profile of the bone engaging component 20, 20', 20" is minimized. The shaft portion 50, 50', 50" may be welded W to the bone contacting component 20, 20', 20" by any appropriate welding process now or hereafter known including but not limited to laser welding, electron beam welding, resistance stud welding, etc. As will be appreciated by one of ordinary skill in the art, the shaft portion 50, 50', 50" of the load carrier engaging component 40, 40', 40" may be welded W to the bone engaging component 20, 20', 20" with or without the incorporation of a press-fit or some other means for coupling. Moreover, the press-fit may be incorporated with or without the textured surfaces 80 (e.g., the radial and/or longitudinal ridges or lamellas 82, 84).

As previously mentioned, the head portion 42, 42', 42" preferably also includes a driving element 60 for engaging a corresponding tip 62 formed on a drive tool 64, such as a screw driver for rotating the dynamic bone fixation element 10, 10', 10" into engagement with the patient's bone or bone fragments B. The driving element 60 may have any form now or hereafter known including, but not limited to, an external hexagon, a star drive pattern, a Phillips head pattern, a slot for a screw driver, a threading for a correspondingly threaded post, an internal recess, etc. It will also be understood by those of skill in the art that the driving element 60 may be of any shape or structure so long as it permits the driving element 60 to drive the dynamic bone fixation element 10, 10', 10" into a desired location in the patient's bone or bone fragments B.

Figure 6B:
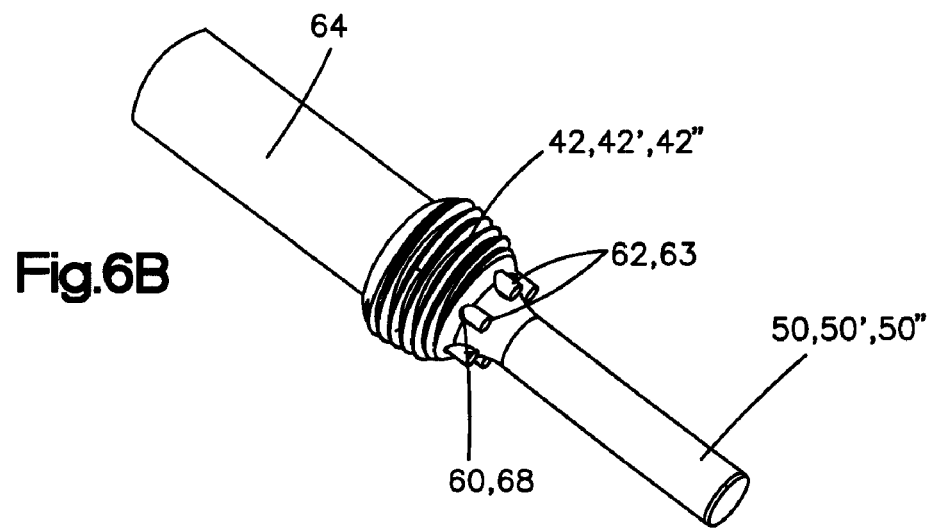
FIG. 6B shows a side view of the drive element coupled to the head portion of the drive tool shown in FIG. 6A.

Preferably, in order to engage the head portion 42, 42', 42" of the load carrier engaging component 40, 40', 40" and to rotate the bone engaging component 20, 20', 20" without slipping or separating the load carrier engaging component 40, 40', 40" from the bone engaging component 20, 20', 20", the head portion 42, 42', 42" of the load carrier engaging component 40, 40', 40" includes a plurality of through holes 68 for receiving a plurality of pins 63 extending from a distal end of the drive tool 64 as best shown in FIGS. 6A and 6B. The plurality of pins 63 being sized and configured to extend through the head portion 42, 42', 42" of the load carrier engaging component 40, 40', 40" and into contact with the bone engaging component 20, 20', 20" so that the plurality of pins 63 contact both the load carrier engaging component 40, 40', 40" and the bone engaging component 20, 20', 20" such that rotation of the drive tool 64 simultaneously rotates both the load carrier engaging component 40, 40', 40" and the bone engaging component 20, 20', 20".

Figure 6C:
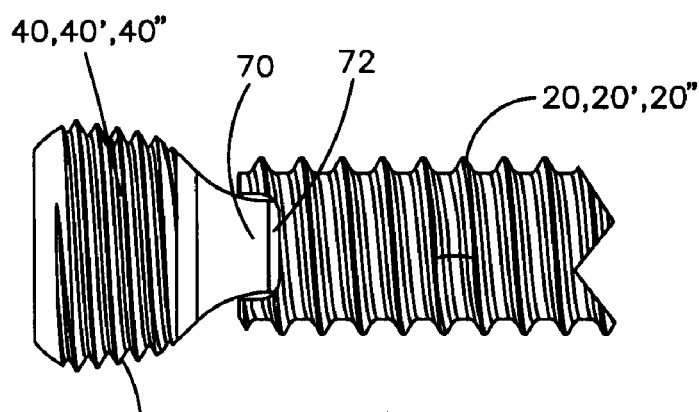
FIG. 6C shows a side view of a drive element for coupling a head portion of a dynamic bone fixation element to a drive tool in accordance with a second preferred embodiment of the present invention.

Alternatively, as best shown in FIG. 6C, the head portion 42, 42', 42" of the load carrier engaging component 40, 40', 40" may include one or more projections 70 extending therefrom and the bone engaging component 20, 20', 20" may include one or more recesses 72 formed therein so that the projection 70 extends into the recess 72 so that rotation of the drive tool 64 simultaneously rotates both the load carrier engaging component 40, 40', 40" and the bone engaging component 20, 20', 20". Preferably, the recess 72 has a length larger than the length of the projection 70 so that some initial rotation of the head portion 42, 42', 42" is permitted prior to the projection 70 contacting the recess 72. As will be appreciated by one of ordinary skill in the art, the recess 72 may be formed on the head portion 42, 42', 42" and the projection 70 may be formed on the bone engaging component 20, 20', 20".

Figure 7:
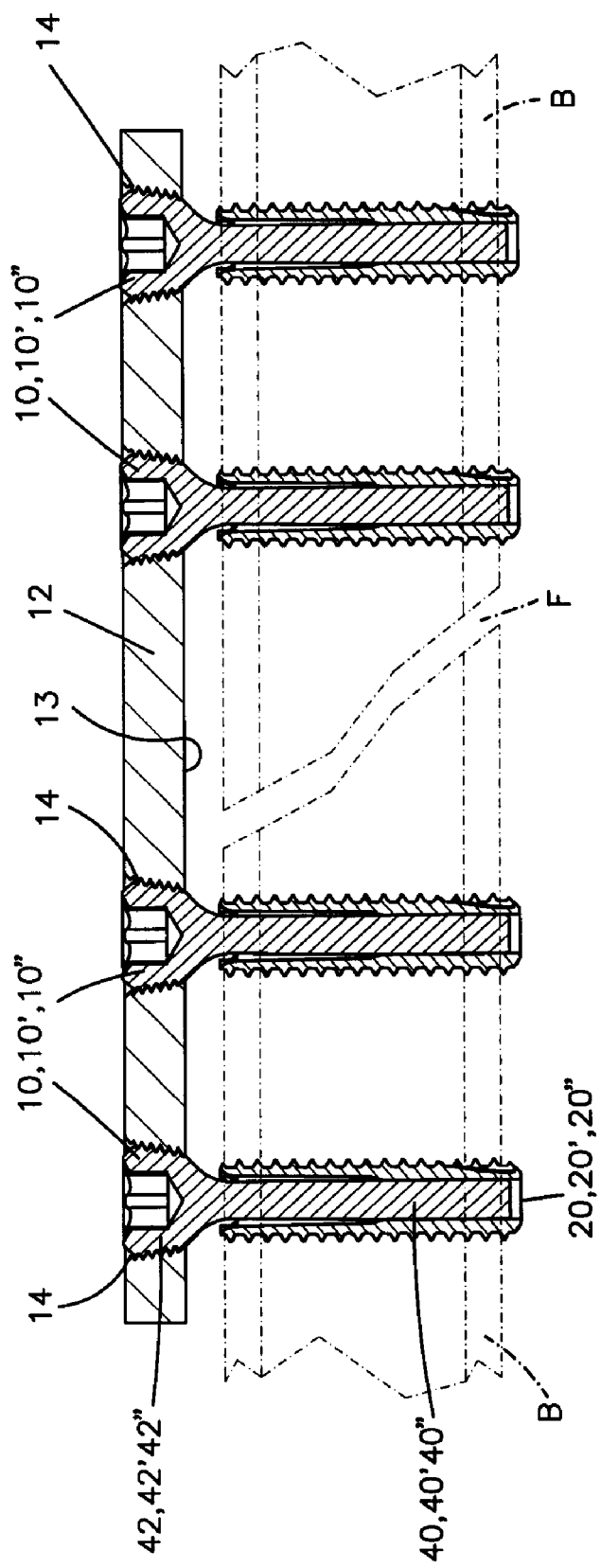
FIG. 7 shows a cross section view of the dynamic bone fixation elements interconnecting a load carrier to a patient's bone.

In use, as best shown in FIG. 7, the dynamic bone fixation element 10, 10', 10" may fix bones or bone fragments B of a broken bone to one another by coupling a load carrier 12 such as a plate to a patient's bone or bone fragments B via two or more dynamic bone fixation elements 10, 10', 10". In an exemplary embodiment, the load carrier 12 may be a plate that is positioned along the bone B such that it extends across a fracture F separating the bone fragments B from one another. Once the load carrier 12 has been appropriately positioned, a dynamic bone fixation element 10, 10', 10" may be inserted into a first opening 14 formed in the plate 12 until the head portion 42, 42', 42" engages the first opening 14 and the bone engaging component 20, 20', 20" engages the first bone fragment B on one side of the bone fracture F. A second dynamic bone fixation element 10, 10', 10" may be inserted into a second opening 14 formed in the plate 12 in substantially the same manner as described above such that the second dynamic bone fixation element 10, 10', 10" engages the second bone fragment B. Thus, the dynamic bone fixation element 10, 10', 10" may be used to fix bone fragments B to one another. It will be understood by those of skill in the art that any number of dynamic bone fixation element 10, 10', 10" may be used to attach the load carrier 12 to the bone or bone fragments B.

Exemplary Surgical Procedure/Method

Generally speaking, the human bone B is formed by a hard, thinner cortical outer portion surrounding a softer cancellous inner portion so that when view in cross-section, the human bone B includes a first layer of cortical bone, an intermediate layer of cancellous bone and a second layer of cortical bone. Rigid fixation generally includes the fixation of one or more bone screws on either side of a fracture F formed in the bone B. In use resulting stress on the fractured bone B causes bending of the bone B and plate 12 which, in turn, results in compression of the second layer of cortical bone (e.g., layer of cortical bone farthest from the plate 12). With standard bone screws 5 there is substantially zero movement in the plate 12 since the plate 12 is too rigid it can not be compressed in a way that permits movement within the first layer of the cortical bone (e.g., layer of cortical bone nearest the plate 12), as such, generally speaking, there is clinically no forming of callus in the first layer of cortical bone. However, incorporation of dynamic bone fixation elements 10, 10', 10" enable the first layer of the cortical bone (e.g., layer of cortical bone nearest the plate 12) to move and hence facilitate the formation of callus in both the first and second layers of cortical bone. That is, incorporation of dynamic bone fixation elements 10, 10', 10" enable parallel movement of the bone fragments B with respect to one another which in turn results in micro-movement of both layers of the cortical bone and hence facilitates the formation of callus in both the first and second layers of cortical bone.

More specifically, referring to FIGS. 8 and 9, an exemplary procedure for internal long bone fixation in accordance with one aspect of the present invention involves using two or more dynamic bone fixation elements 10, 10', 10" on either side of a fracture F so that the resulting movement of the head portion 42, 42', 42" of the load carrier engaging component 40, 40', 40" with respect to the bone engaging component 20, 20', 20" enables, in addition to bending, parallel movement of the bone or bone fragments B across the fracture F. Thus, by incorporating two or more dynamic bone fixation elements 10, 10', 10" on both sides of the fracture F, the preferred exemplary surgical procedure enables better healing across the fracture F as the bone/bone fragments B on either side of the first layer of cortical bone (e.g., layer of cortical bone nearest the plate 12) remain in constant contact which is contrary to prior art rigid fixation systems wherein the bone B is subjected to bending stress only. That is, when used in connection with an internal trauma application, when two or more dynamic bone fixation elements 10, 10', 10" are attached to a single bone or bone fragment B, the shaft portion 50, 50', 50" is forced to adopt a generally "S" shaped configuration generally parallel to one another to accommodate the micro-movements of the attached bone or bone fragment B.

When contrasted with external dynamic fixation such as, for example, via external Schanz screws, internal dynamic fixation is completely internal thereby reducing the risk of infection generally associated with external Schanz screws. In addition, with internal dynamic bone fixation, the bone-screw interface of the dynamic bone fixation elements 10, 10', 10" remain motionless because all of the dynamic motion occurs within the lumen 28, 28', 28". In contrast, with external dynamic bone fixation, the S-bending in the external Schanz screws occurs along the length of the screw that forms the bone-screw interface so that bending in the external Schanz screws gradually weakens the adherence of the screw in the bone.

Incorporation of a single dynamic bone fixation element 10, 10', 10" on either side of the fracture F is insufficient since using a single dynamic bone fixation element 10, 10', 10" on either side of the fracture F permits each of the bone fragments B to bend towards the load carrier 12 (e.g., angulation between the plate 12 and the bone B is permitted). The bone fragments B are allowed to rotate around the screw axis. In addition, using a single dynamic bone fixation element 10, 10', 10" on either side of the fracture F permits the dynamic bone fixation elements 10, 10', 10" to bend. Thus, using a single dynamic bone fixation element 10, 10', 10" on either side of the fracture F decreases the overall stability of the construct during bone healing.

Alternatively, a second embodiment of an exemplary surgical procedure as best shown in FIG. 10 may be carried out using two or more dynamic bone fixation elements 10, 10', 10" on one side of the fracture F while standard bone screws 5 may be used on the other side of the fracture F. Incorporation of standard bone screws 5 on one side of the fracture is particularly beneficial wherein, for one reason or another, the surgeon needs or desires to limit movement of the fractured bone to one side of the fracture only.

Alternatively and/or in addition, a third embodiment of an exemplary surgical procedure as best shown in FIGS. 11A and 11B involves using one or more standard bone screws 5 on one or both sides of the fracture F so that micro-movement of the bone/bone fragments B is prevented for some length of time. That is, for example, one or more standard bone screws 5 may be used on one or both sides of the fracture F so that for some initial period of time, for example, two or three weeks, micro-movement of the bone or bone fragments B is prevented so that the fracture site can be initially stabilized to facilitate initial callus formation. That is, days after initial fixation, tissue and/or cells may replicate and transform so that the cells on either side of the fracture develop until they unite with their counterparts from the other side of the fracture. Eventually, the fracture F is bridged, restoring some of the bone's original strength. Thereafter, removal of the standard bone screws 5 from the surgical construct enables micro-movement of the bone/bone fragments B and/or enables distraction of the bone/bone fragments F. In addition, incorporation of one or more standard bone screws 5 may be used on one or both sides of the fracture F so that in cases of non-union, the bone or bone fragments B may be readjusted, repositioned, or alternative fixation may be applied.

Alternate Embodiments of the Dynamic Bone Fixation Element

Figure 12:
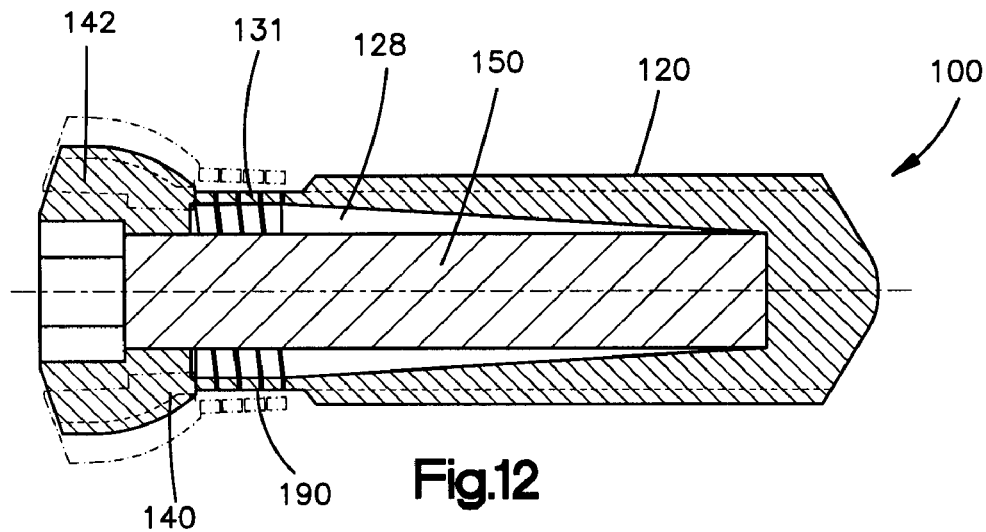
FIG. 12 shows a cross-sectional view of a dynamic bone fixation element according to a fourth exemplary embodiment of the present invention.

Referring to FIG. 12, the dynamic bone fixation element 100 of a fourth preferred embodiment may be in the form of an integrally formed dynamic bone fixation element. That is, the load carrier engaging component 140 may be integrally formed with the bone engaging component 120 so that the shaft portion 150 may be integrally formed with the load carrier engaging component 140 and the bone engaging component 120. The dynamic bone fixation element 100 of the fourth preferred embodiment may achieve flexibility via the lumen 128 formed in the dynamic bone fixation element 100. That is, due to the size and configuration of the shaft portion 150 and the lumen 128 formed in the bone engaging component 120, the head portion 142 is able to flex and/or move with respect to the bone engaging component 120.

In addition and/or alternatively, the dynamic bone fixation element 100 of the fourth preferred embodiment may achieve flexibility via various designs of a neck portion 131 (e.g., area between the bone engaging component 120 and the load carrier engaging component 140). Preferably, material in the area of the neck 131 is removed in order to reduce structural stiffness. As a result of the removal of this material, the dynamic bone fixation element 100 becomes increasingly more flexible. For example, the dynamic bone fixation element 100 may be formed with one or more slots 190 in the neck portion 131. Slot(s) 190 may be formed in the neck portion 131 so that the neck 131 can function as a spring, allowing the neck portion 131 to flex, thereby allowing the head portion 142 to move with respect to the bone engaging component 120. The shape of the slot 190 formed in the neck portion 131 may be configured to take the form of any one of a plurality of shapes and profiles. Different profiles may be provided to control axial and rotational movement. For example, a helical spring profile allows axial movement but generally does not block screw rotation, whereas a rectangular profile allows axial movement and generally blocks screw rotation. Alternatively, a V-shaped spring profile blocks screw rotation and generally limits axial motion. The spring constant of the material and shape of the slots 190 formed in the neck portion 131 of the dynamic bone fixation element 100 may be used to control the movement of the head portion 142.

In addition, additional element such as, for example, chamfers, conical openings, stiff pins, etc. may be incorporated as motion limitation means.

Figure 13:
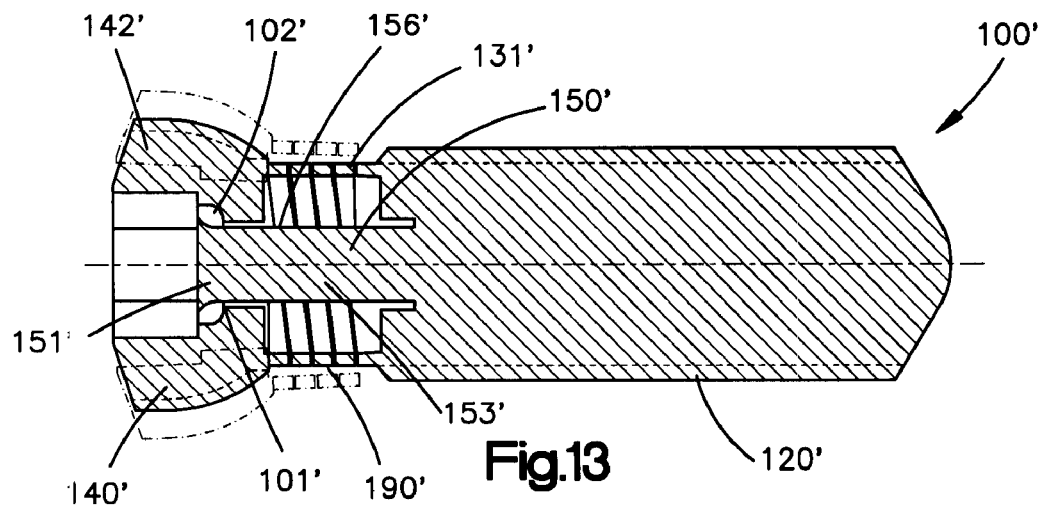
FIG. 13 shows a cross-sectional view of a dynamic bone fixation element according to a fifth exemplary embodiment of the present invention.

Referring to FIG. 13, the dynamic bone fixation element 100' of a fifth preferred embodiment may include a hollow volume 101' formed in and through the neck portion 131' such that a feather pin 150' may be located inside of the hollow volume 101'. In use, the feather pin 150' is similar to the shaft portion previously described however the feather pin 150' may not be coupled to or engage both the bone engaging component 120' and the load carrier engaging component 140'. The feather pin 150' may be, for example, integrally formed with the bone engaging component 120'. The feather pin 150' may extend from the bone engaging component 120' through the hollow volume 101' of the neck portion 131' and into the head portion 142' of the load carrier component 140'. A gap 102' is preferably provided between the outer surface 156' of the feather pin 150' and the head portion 142'. As shown, the feather pin 150' preferably includes a head portion 151' and a body portion 153' with the head portion 151' having a larger diameter than the body portion 153'. The neck portion 131' of the dynamic bone fixation element 100' preferably includes a plurality of slots 190', as previously described in connection with dynamic bone fixation element 100. In use, the flexibility, both axial and compressive, is provided by the slots 190' formed in the neck portion 131' of the dynamic bone fixation element 100'. The flexibility may be limited by the size of the feather pin 150' and the gap 102' between the feather pin 150' and the head portion 142' of the dynamic bone fixation element 100' such that when the dynamic bone fixation element 100' is compressed, extended or moved axially, the feather pin 150' acts as a stop and limits the motion generally where, and when, the feather pin 150' contacts the interior walls of the head portion 142'.

Figure 14:
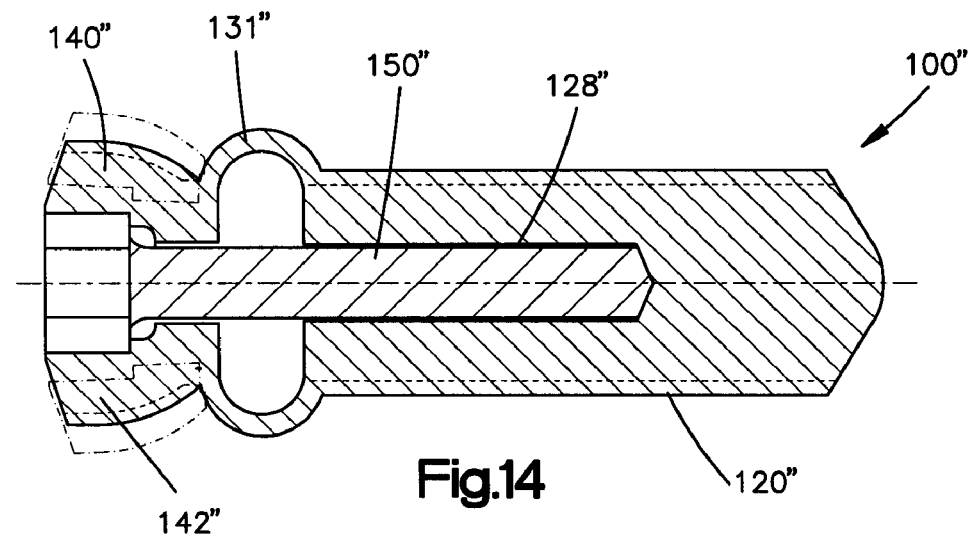
FIG. 14 shows a cross-sectional view of a dynamic bone fixation element according to a sixth exemplary embodiment of the present invention.

Referring to FIG. 14, the dynamic bone fixation element 100" of a sixth preferred embodiment may include a feather pin 150" that is not integrally formed with the dynamic bone fixation element 100" but rather coupled to a lumen 128" formed in the bone engaging component 120". The feather pin 150" may be coupled to the lumen 128" formed in the bone engaging component 120" by any means as previously described. Furthermore, the neck portion 131" of the dynamic bone fixation element 100" may be formed as a thin-walled hollow convex projection or bellow type structure which preferably functions as a spring to provide elasticity and/or flexibility. The hollow convex projection or bellow type structure may be further filled with a damper material to preferably control flexibility and protect the structural integrity of the dynamic bone fixation element 100". The feather pin 150" may be optional and may be removed from the dynamic bone fixation element 100".

Figure 15:
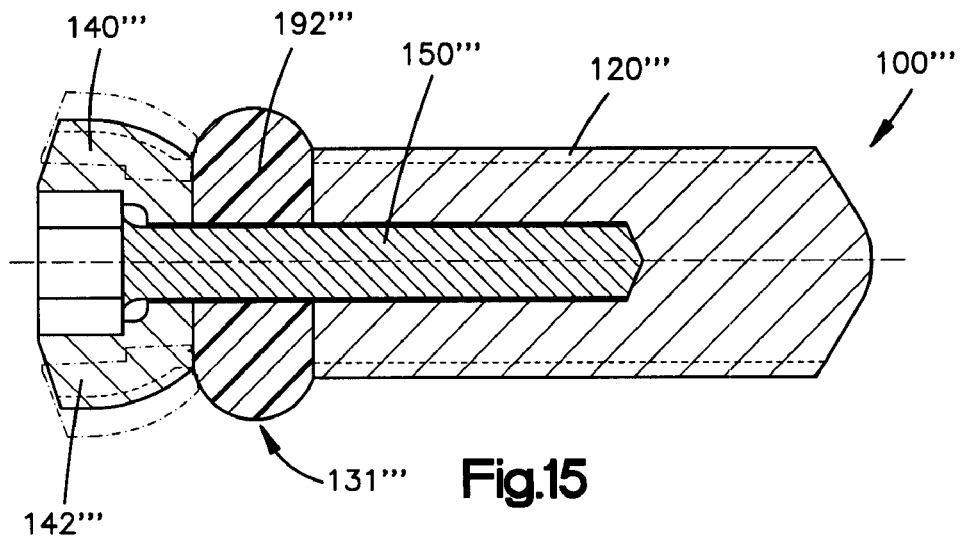
FIG. 15 shows a cross-sectional view of a dynamic bone fixation element according to a seventh exemplary embodiment of the present invention.

Referring to FIG. 15, the dynamic bone fixation element 100''' of a seventh preferred embodiment may include a damper material or an elastic element 192''' in the neck portion 131''' (e.g., between the head portion 142''' and the bone engaging portion 120''') of the dynamic bone fixation element 100'''. A feather pin 150''' preferably extends through the damper material or elastic element 192'''. The damper material or elastic element 192''' may be fixed, axially movable or rotatable with respect to the feather pin 150'''. In use, the damper material or elastic element 192''' acts as a damper.

With respect to the fifth, sixth and seventh embodiments of the dynamic bone fixation element (as shown in FIGS. 13-15), it should be noted that the feather pin 150', 150", 150''' may be sized and configured to be any number of shapes and sizes. For example, the feather pin 150', 150", 150''' may include a head portion which may be cylindrical, conical, etc., and the body portion may be longer or shorter and may be tapered. Furthermore, the lumen formed in the dynamic bone fixation element may be sized and configured to any number of different shapes and sizes, for example it may be cylindrical, or it may be tapered, etc. Furthermore, it should be noted that while the ends of the feather pin 150', 150", 150''' are shown to be substantially circular, they may take on any geometric profile such as, for example, polygon.

Figure 16A:
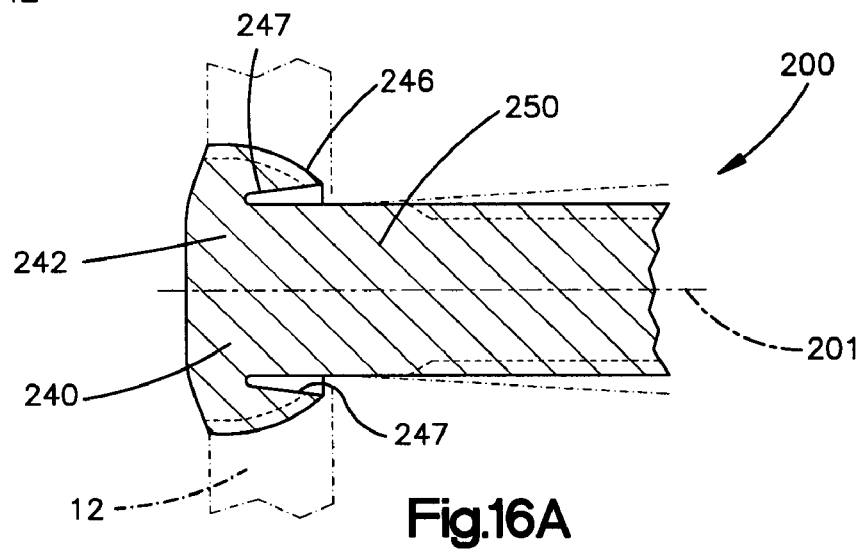
FIG. 16A shows a first detailed, cross-sectional view of a head portion of a dynamic bone fixation element according to an eighth exemplary embodiment of the present invention.
Figure 16B:
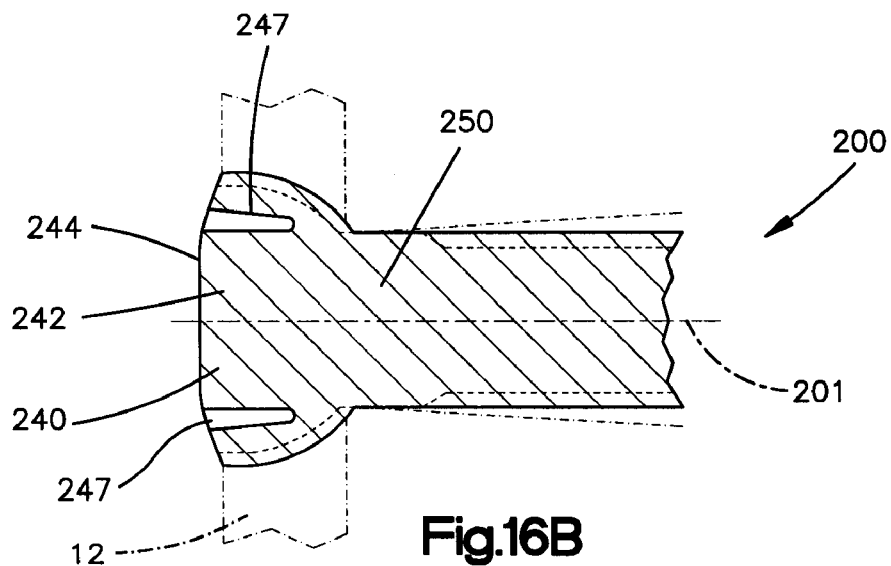
FIG. 16B shows a second detailed, cross-sectional view of a head portion of a dynamic bone fixation element according to the eighth exemplary embodiment of the present invention.
Figure 16C:
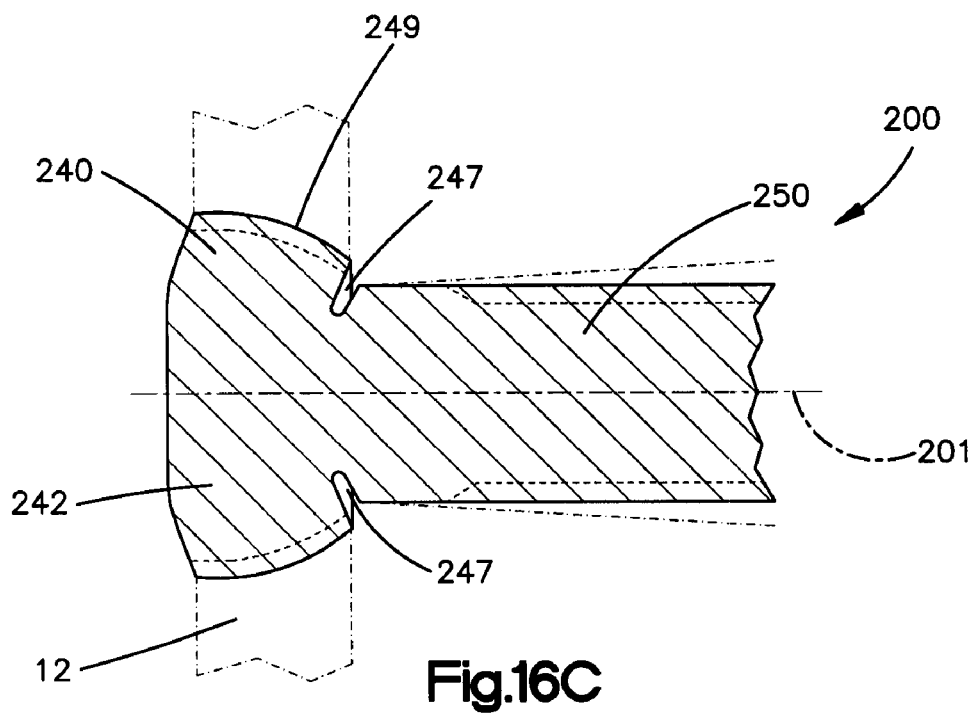
FIG. 16C shows a third detailed, cross-sectional view of a head portion of a dynamic bone fixation element according to the eighth exemplary embodiment of the present invention.

Referring to FIGS. 16A-16C, the dynamic bone fixation element 200 of an eight preferred embodiment may include one or more slots 247 formed in the head portion 242 of the load carrier engaging component 240. The slots 247 may extend into the head portion 242 from a distal end 246 of the head portion 242 (as shown in FIG. 16A). Alternatively, the slot 247 may extend into the head portion 242 from a proximal end 244 of the head portion 242 (as shown in FIG. 16B). Alternatively, the slot 247 may extend from a circumferential edge 249 of the head portion 242 towards the longitudinal axis 201 of the dynamic bone fixation element 200 (as shown in FIG. 16C). The slot 247 may be substantially parallel to the longitudinal axis 201 of the dynamic bone fixation element 200 or may be angled with respect to the longitudinal axis 201 of the dynamic bone fixation element 200. Alternatively and/or in addition, the slot 247 may be tapered, or alternatively the slot 247 may be straight or some other configuration. In use, the head portion 242 may flex, with the size, taper, and location of the slot 247 defining the range of flexibility. It should be appreciated that the slots 247 may be modified to fit a particular use of a dynamic bone fixation element 200, for example a slot 247 may have a larger or a smaller taper, it may extend less or farther into the head portion 242, it may be angled to any degree, and multiple slots 247 may be used.

Figure 17:
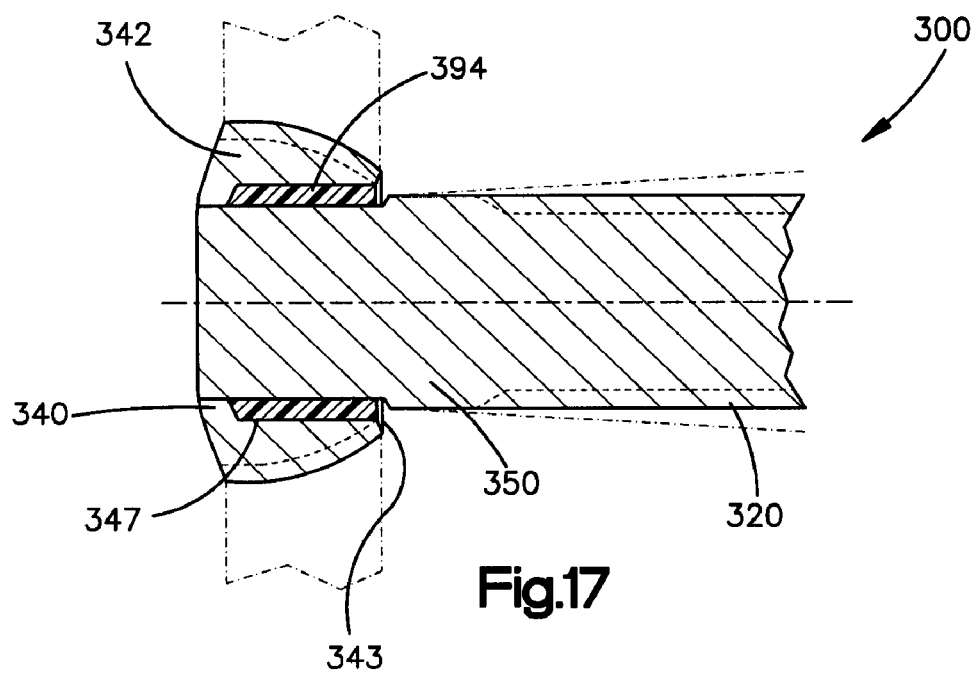
FIG. 17 shows a partial cross-sectional view of a dynamic bone fixation element according to a ninth exemplary embodiment of the present invention.

Referring to FIG. 17, the dynamic bone fixation element 300 of a ninth preferred embodiment may include a multi-piece head assembly thereby preferably forming one or more slots 347 in the head portion 342. The multi-piece head assembly preferably includes a head portion 342, a body portion 350 and an optional damper material 394. The head portion 342 preferably includes an aperture 343 through which the body portion 350 is preferably inserted and to which it is preferably coupled. The head portion 342, aperture 343 and body portion 350 all being sized and configured so that one or more slots or gaps 347 are formed between the head portion 342 and the body portion 350. The one or more slots or gaps 347 are preferably filled with the damper material 394. It should be appreciated that depending on the use for which the dynamic bone fixation element 300 is intended, any type of slot or gap 347 may be incorporated into the head portion 342, and any amount of damper material 394 may be used. In addition, or alternatively the slot or gap 347 may be partially filled or completely filled with the damper material 394. Further, it should be appreciated that coupling of the body portion 350 to the head portion 342 may be performed by any method including, but not limited to press fitting, a threaded connection, welding, pinning, shrinking, engrailing, etc. In addition, polymeric components or reduced structures such as flat springs, disk springs, meander shaped flat springs, etc. may also be incorporated.

The dynamic bone fixation elements 10, 10', 10", 100, 100', 100", 100''', 200, 300 (collectively 10-300) of the preferred embodiments may be manufactured from any biocompatible material now or hereafter known in the art including but not limited to titanium, a titanium alloy, stainless steel, etc. In addition, the dynamic bone fixation elements 10-300 of the preferred embodiments may be coated to facilitate osseo-integration. For example, the bone engaging component 20, 20', 20", 120, 120', 120", 120''', 220, 320 (collectively 20-320) may be coated, for example, with a hydroxylapatite, or its outer surface may be roughened, perforated or subjected to surface treatments such as, for example, anodic-plasma-chemical to embed hydroxylapatite into the titanium-oxide surface layer. Alternatively and/or in addition, the dynamic bone fixation elements 10-300 of the preferred embodiments may be coated to enable one or more semi- or non-biocompatible materials to be used such as, for example, nickel, a nickel alloy, Ni—Ti-alloy (e.g., Nitinol), stainless steel, a memory shaped alloy, cobalt chromium (CoCr) or a cobalt chromium alloy such as, for example, CoCrMo, CoCrMoC, CoCrNi, CoCrWNi, etc. For example, the bone engaging component 10-300 may be manufactured from cobalt chromium molybdenum and the outer threads may or may not be plasma coated with pure titanium.

The bone engaging 20-320 and load carrier engaging component 40, 40', 40", 140, 140', 140", 140''', 240, 340 (collectively 40-340) may be manufactured from the same material. Alternatively, the bone engaging component 20-320 may be manufactured from a different material than the load carrier engaging component 40-340. For example, the bone engaging component 20-320 may manufactured from a biocompatible metal, more preferably one that is easily processible so that, for example, the external bone thread may be milled such as, for example, titanium, a titanium alloy, such as TAV (Ti-6Al-4V) or TAN (Ti-6Al-7Ni). The load carrier engaging component 40-340 may be made from a high strength material (e.g., $R_p$ 0.2>1,000 MPA) in order to provide high elasticity and maximum stability. In addition, the load carrier engaging component 40-340 is preferably manufactured from a material that provides resistance to fretting within the head-plate interface. The load carrier engaging component 40-340 may be made from, for example, a strong metal or metal alloy, such as CoCrMo, CoCrMoC, CoCrNi or CoCr-WNi. In one particularly preferred embodiment, the bone engaging component 20-320 is made from titanium or a titanium alloy such as, for example, TAV or TAN while the load carrier engaging portion 40-340 is made from cobalt chromium (CoCr).

The damper materials used in some of the above exemplary embodiments may be any material now or hereafter known in the art with damping properties including, but not limited to polymers, silicone, urethane, polycarbonate-urethane (PCU), elastic members of the polyaryletherketone (PAEK) family, elastic members of poly-esther-ether family, hydrogels, co-polymers, etc. The precise type and amount of damper material may be chosen based on the elasticity of the damping required.

It will also be understood by those of skill in the art that the use of strong metals and metal alloys in the dynamic bone fixation device 10-300 prevents the galling of the dynamic bone fixation device 10-300 to the load carrier 12. Drive damage is also prevented such that corrections of the load carrier 12 may be easily made.

The dynamic bone fixation elements 10-300 may be formed so that they deform elastically when subjected to external forces as a result of micro-movement of the bone or bone fragments B to which they are coupled. Thus, if later micro-movements of the bone or bone fragments B are directed back toward an original position, the dynamic bone fixation elements will spring back to their original positions. Alternatively, the dynamic bone fixation elements 10-300 may be formed to plastically deform by the forces exerted during micro-movement of the bone or bone fragments B so that the dynamic bone fixation elements 10-300 retain their deformed shapes even after the forces imposed by the micro-movements have been removed. The dynamic bone fixation elements 10-300 may be formed to deform with a substantially uniform spring constant (e.g., a force twice as great produces twice the deformation). Alternatively, the dynamic bone fixation elements 10-300 may be formed to remain substantially unflexed at all times until a force exerted by the micro-movements exceeds a predetermined limit.

Generally speaking, in use movement of the load carrier engaging component is preferably non-linear. More specifically, the shaft portion is preferably designed as a bendable pin so that the shaft portion is capable of moving with respect to the bone engaging component and able to give within a limited range. Referring to FIG. 3A, in an exemplary embodiment of the dynamic bone fixation element and in order to optimize the dynamic bone fixation element for maximum insertion torque versus elasticity of the shaft portion, the ratio of the outer diameter of the bone engaging component to displacement is between about 10 to about 20, and more preferably about 15. The ratio of the outer diameter of the bone engaging component to the outer diameter of the shaft portion is between about 1.4 to about 2.2, more preferably 1.8. The ratio of the outer diameter of the bone engaging component to the effective flexible length of the shaft portion is between about 3.5 to about 5.5, more preferably 4.6. Exemplary sizes for the bone engaging component and load carrier engaging component are illustrated in Table 1.

TABLE 1

Exemplary Dimensions

| Outer Diameter of Bone Engaging Component (d) | Length of Bone Engaging Component (l) | Total Displacement (e) | Outer Diameter of the Shaft Portion (d1) | Effective Flexible Length (lf) |
|---|---|---|---|---|
| 3.50 mm | 26.00 mm | +/−0.20 mm | 2.00 mm | 17.00 mm |
| 5.00 mm | 34.00 mm | +/−0.30 mm | 3.00 mm | 25.00 mm |
| 6.20 mm | 36.00 mm | +/−0.50 mm | 3.40 mm | 23.00 mm |
| 6.20 mm | 46.00 mm | +/−0.50 mm | 3.40 mm | 30.00 mm |

Dynamic Pedicle Screw Fixation Clamps

Pedicle screw fixation clamps are often used when bony structures, such as facet joints or osteophites, would prevent a straightforward fixation of a rod into a pedicle screw. As a result, fixation clamps may be used to bridge around such hurdles. In these cases it may be advantageous to provide elasticity in the fixation clamps through, for example, the incorporation of a damper. For example, the damper may be in the form of an elastic or polymeric component such as PCU, silicone, rubber, etc. Alternatively, the damper may be in the form of a spring such as flat springs, disk springs, meander shaped flat springs, etc.

Referring to FIGS. 18A and 18B, the dynamic pedicle screw fixation clamp 500 of a first preferred embodiment may include a bone screw 502 and a frame 510. The frame 510 preferably includes a pedicle screw clamping assembly 520 and a rod clamping assembly 530. The pedicle screw clamping assembly 520 preferably includes a clamping sleeve 522, a collet 524, and a locking mechanism 526 to secure and/or lock the position of the bone screw 502 with respect to the frame 510, although other configurations for the pedicle screw clamping assembly 520 are contemplated.

The rod clamping assembly 530 may be offset or located to the side of the pedicle screw clamping assembly 520. The rod clamping assembly 530 preferably includes a recess 532, a clamp portion 534, a locking cap portion 536 and a damper 550. The clamp portion 534 is preferably shaped like a pedestal and includes a rod-receiving portion 542 attached to a column portion 540. The rod-receiving portion 542 preferably has a perimeter larger than the circumference of the column portion 540. Additionally, the rod-receiving portion 542 preferably has a length or perimeter that is slightly larger than the diameter of the recess 532 formed in the frame 510. The column portion 540 is preferably sized and configured to be inserted into the recess 532 formed in the frame 510 so that there is a clearance or gap between the outer surface of the column portion 540 and the inner surface of the recess 532. Additionally, the column portion 540 preferably has a height that is slightly larger than the height of the recess 532 formed in the frame 510 so that there is a clearance or gap between the bottom surface of the rod-receiving portion 542 and the top surface of the frame 510. Preferably the gap between the outer surface of the column portion 540 and the inner surface of the recess 532 and the gap between the bottom surface of the rod-receiving portion 542 and the top surface of the frame 510 is filled with the damper 550, more preferably a damper material.

The damper 550 is preferably annularly shaped and inserted into the recess 532 formed in the frame 510. The column portion 540 is preferably inserted into the recess 532 and through a hollow cavity formed in the damper 550 so that the column portion 540 is surrounded by the damper 550. The frame 510 may also include an aperture 545 formed in the bottom surface thereof in communication with the recess 532, the aperture 545 being sized and configured to receive an end 542 of the column portion 540. Preferably there is a clearance or gap between the end 542 of the column portion 540 and the inner circumference of the aperture 545. The damper material 550 preferably is press-fitted or injection molded into the recess 532 formed in the frame 510. Alternatively, the damper 550 may be press-fitted or injection molded into another frame (not shown), which in turn would be press-fitted into the recess 532 formed in the frame 510.

In use, a rod 504 is preferably placed into the rod-receiving portion 542 and clamped therein by the locking cap 536. In this position, the rod 504 is free to move with respect to the frame 510 and with respect to the pedicle screw 502 due to the flexibility of the damper 550. Preferably, the clamp portion 534 is sized and configured to contact the frame 510 once the dynamic pedicle screw fixation clamp 500 has reached a maximum angle of desired flex.

Figure 18C:
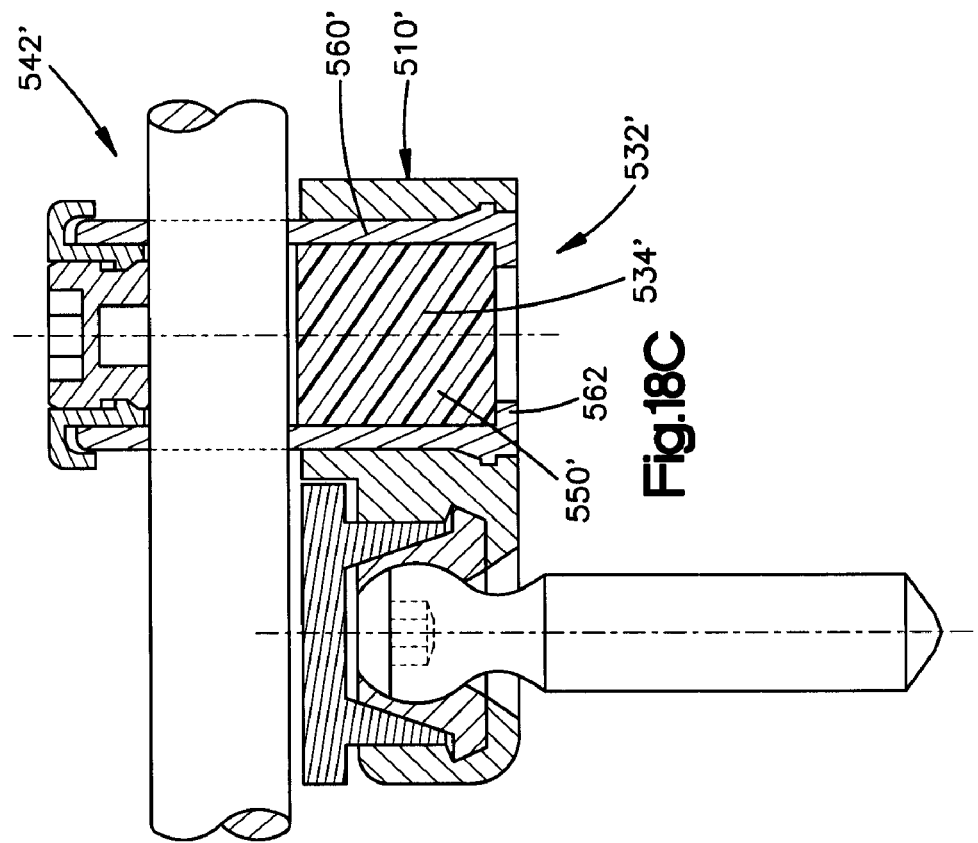
FIG. 18C shows a cross-sectional view of an alternate embodiment of the dynamic pedicle screw fixation clamp shown in FIG. 18A.

Alternatively, as shown in FIG. 18C, the clamping portion 534' may have a rod receiving portion 542' and an extension portion 560', the extension portion 560' may be a hollow cylindrical element that includes a plurality of slots forming flexible tabs 562'. In use, the flexible tabs 562' are inserted into the recess 532' formed in the frame 510'. The interior volume of the flexible tabs 562' is preferably filled with the damper 550'. In use, the slots provide additional flexibility to the clamping portion 534' so that the bottom portion of the clamping portion 534' along with the damper 550' permits movement of the rod 502' due to the flexibility of the damper 550' and the resulting flexing of the tabs 562'. In some embodiments, the rod-clamping portion 542' may be rotatable within the recess 532' formed in the frame 510'.

Figure 19:
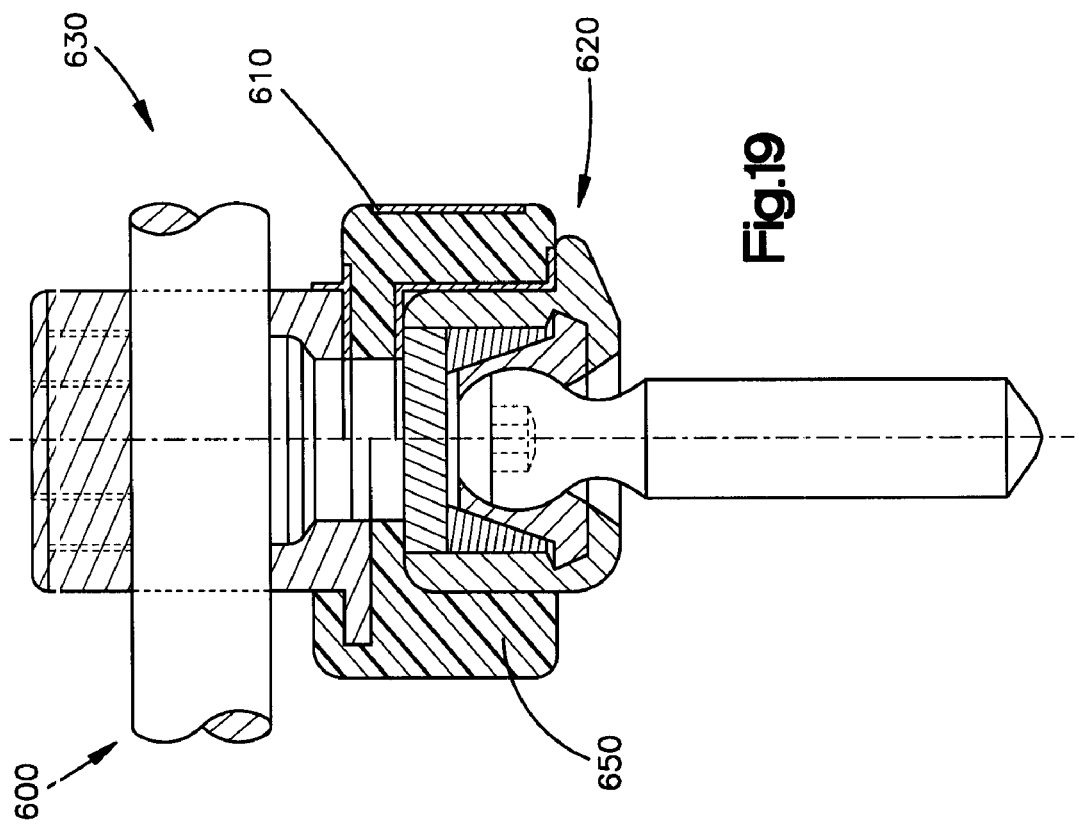
FIG. 19 shows a cross-sectional view of a dynamic pedicle screw fixation clamp according to a second exemplary embodiment of the present invention.

Referring to FIG. 19, the dynamic pedicle screw fixation clamp 600 of a second preferred embodiment may include a pedicle screw clamping assembly 620 and a rod clamping assembly 630 wherein the pedicle screw clamping assembly 620 and the rod clamping assembly 630 are in vertical alignment, as opposed to the side-by-side configuration of the first preferred embodiment. A damper 650, more preferably a damper material, is preferably located in between the pedicle screw clamping assembly 620 and the rod clamping assembly 630 so that flexibility is provided between the pedicle screw clamping assembly 620 and the rod clamping assembly 630. Alternatively, the damper 650 may interconnect the pedicle screw clamping assembly 620 and the rod clamping assembly 630. The damper 650 may be fixed between the pedicle screw clamping assembly 620 and the rod clamping assembly 630 by any mechanism including, for example, via a frame, a ring, etc. Preferably, the damper 650 is injection molded into and around the frame or ring 610 to connect the pedicle screw clamping assembly 620 and the rod clamping assembly 630 together (as shown in the left side of FIG. 19).

Figure 20A:
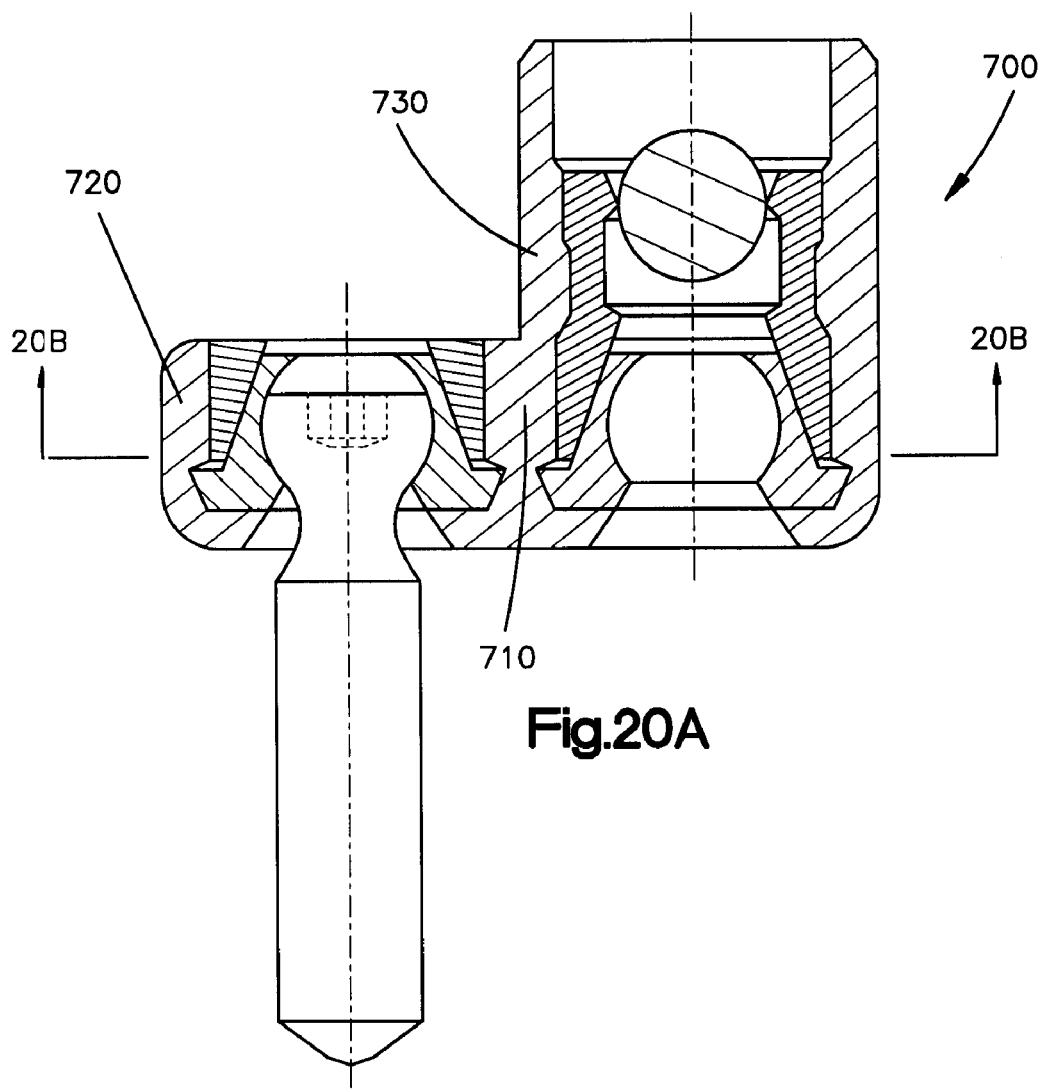
FIG. 20A shows a cross-sectional view of a dynamic pedicle screw fixation clamp according to a third exemplary embodiment of the present invention.
Figure 20B:
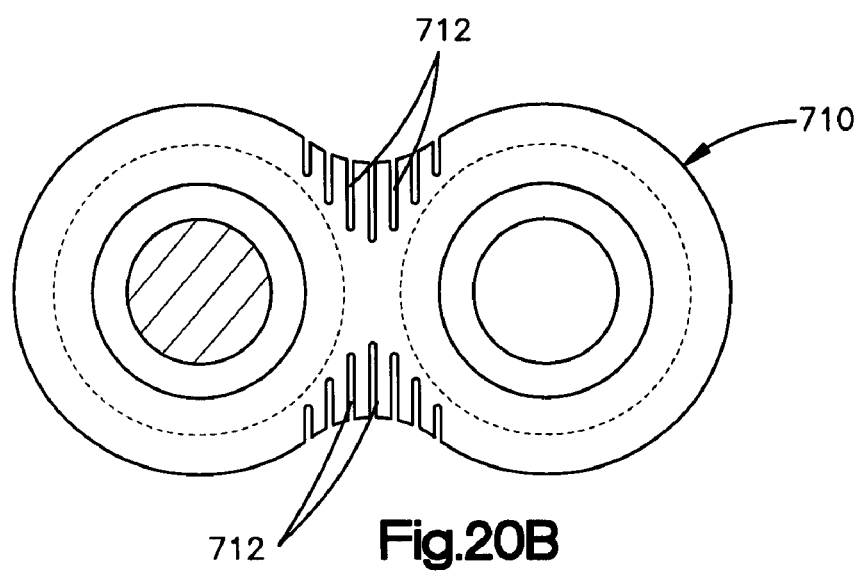
FIG. 20B shows a cross-sectional view of the frame used in connection with the dynamic pedicle screw fixation clamp shown in FIG. 20A taken along line 20B-20B of FIG. 20A.

Referring to FIGS. 20A and 20B, the dynamic pedicle screw fixation clamp 700 of a third preferred embodiment may include a pedicle screw clamping assembly 720 and a rod clamping assembly 730. The rod clamping assembly 730 may be offset or located to the side of the pedicle screw clamping assembly 720 via a frame 710. The frame 710, at the point wherein the pedicle screw clamping assembly 720 connects with rod clamping assembly 730, preferably includes a plurality of slots 712 that provide flexibility between the rod clamp assembly 730 and the screw clamp assembly 720. The slots 712 may take any shape or form as needed for the amount of flexibility that is desired.

Figure 21A:
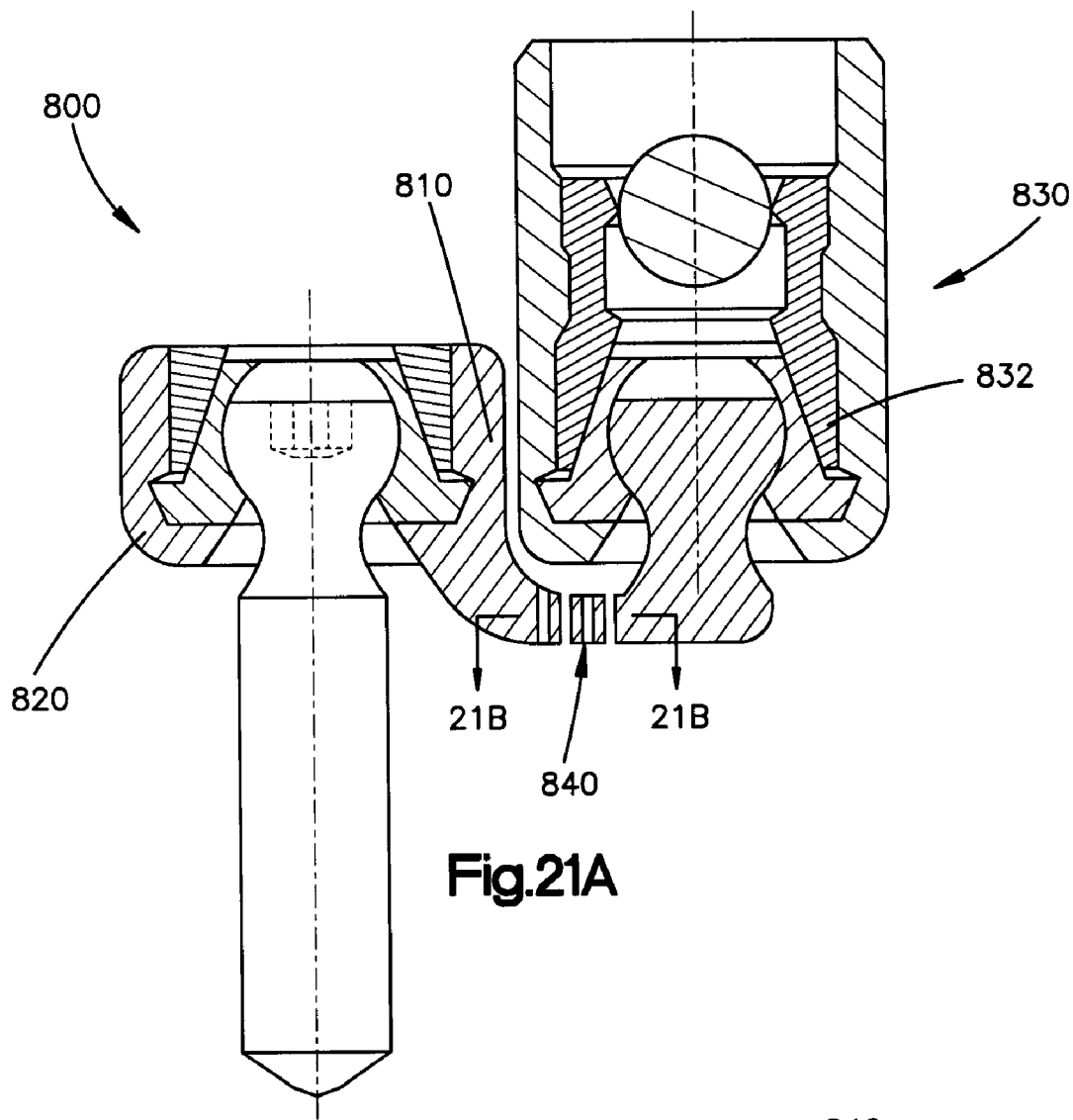
FIG. 21A shows a cross-sectional view of a dynamic pedicle screw fixation clamp according to a fourth exemplary embodiment of the present invention.
Figure 21B:
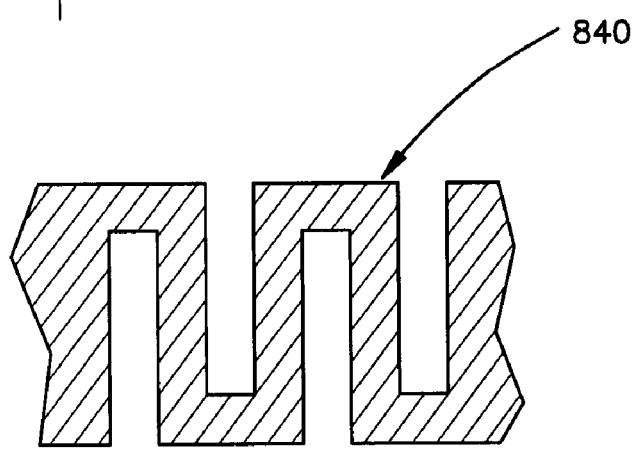
FIG. 21B shows a detailed, cross-sectional view of the dynamic section of the connecting member used in connection with the dynamic pedicle screw fixation clamp shown in FIG. 21A.

Referring to FIGS. 21A and 21B, the dynamic pedicle screw fixation clamp 800 of a fourth preferred embodiment may include a pedicle screw clamping assembly 820 and a rod clamping assembly 830. The rod clamping assembly 830 may be offset or located to the side of the pedicle screw clamping assembly 820 via a connecting member 810. The connecting member 810 preferably includes a dynamic section 840. For example, the dynamic section 840 may be in the form of a spring (as shown in FIGS. 21A and 21B), a damper material, etc. In use, the dynamic section 840 of connecting member 810 allows flexing of the rod clamp assembly 830 with respect to the screw clamp assembly 820. The dynamic section 840 may be sized and configured to provide the level of flexibility that is desired for a particular application. The connecting member 810 may be coupled to the pedicle screw clamping assembly 820 and to the rod clamping assembly 830 by an mechanism know. For example, the connecting member 810 may be coupled to the body of the screw clamp assembly 820 and may be received within a connector clamp 832 located in the rod clamping assembly 830.

Figures 22, 23:
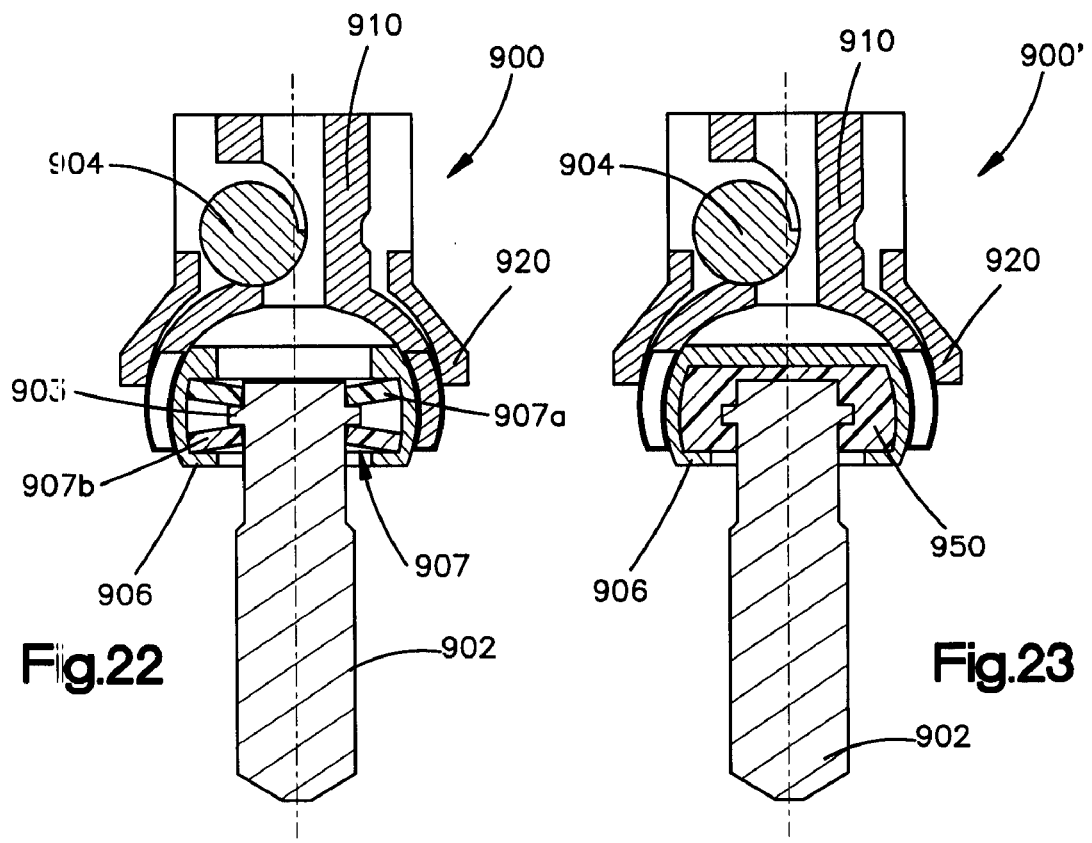
FIG. 22 shows a cross-sectional view of a dynamic pedicle screw fixation clamp according to a fifth exemplary embodiment of the present invention.
FIG. 23 shows a cross-sectional view of an alternate embodiment of the dynamic pedicle screw fixation clamp shown in FIG. 22.

Referring to FIG. 22, the dynamic pedicle screw fixation clamp 900 of a fifth preferred embodiment may include a rod/screw clamping assembly 910, a locking ring 920 and a dynamic bone screw 902. The screw/rod clamping assembly 910 may be a side opening pedicle screw assembly. The dynamic bone screw 902 and the rod 904 are preferably inserted into their respective receiving portions in the rod/screw clamping assembly 910. In use, as will be appreciated by one of ordinary skill in the art, tightening of the rod 904 within the rod receiving portion causes the rod 904 to press down onto the locking ring 920, which in turns causes the screw receiving portion of rod/screw clamping assembly 910 to tighten and clamp the dynamic bone screw 902. The dynamic bone screw 902 however preferably incorporates one or more flexible elements so that the bone screw 902 can move or flex with respect to the rod 904. For example, the dynamic screw 902 may include a head portion 906 that includes a cavity for receiving a pair of beveled spring washers 907. The first beveled spring washer 907*a* preferably is located on the rod-facing end of the dynamic screw 902 with its center angled towards the second beveled spring washer 907*b*, whereas the second beveled spring washer 907*b* preferably is located adjacent to the shaft of the dynamic screw 902 with its center angled towards the first beveled spring washer 907*a*. The dynamic screw 902 preferably also includes a ridge 903 formed thereon, the ridge 903 being received between the two beveled spring washers 907. The ridge 903 is preferably sized and configured to keep the beveled springs washers 907 from slipping.

In use, the beveled spring washers 907 flex, allowing the bone contacting portion to deflect and flex relative to the head portion 906, and hence relative to the remainder of the pedicle screw assembly 900. Although two beveled spring washers 907 are shown and described, other types and amounts of springs are possible. Additionally, the bone screw 902 may be received by the head portion 906 and/or attached to the springs in any number of ways including, but not limited to, welding, gluing, etc. Depending on the type of springs, and method of attachment of the springs that is used, the structure of the screw may be modified. For example, the screw may be configured not to have a ridge, or to include recesses or grooves to receive the springs, etc. Alternatively, as best shown in FIG. 23, the springs of the screw head design may be replaced with a damper material 950, or alternatively the springs in FIG. 22 can be used with a damper material 950.

Figure 24:
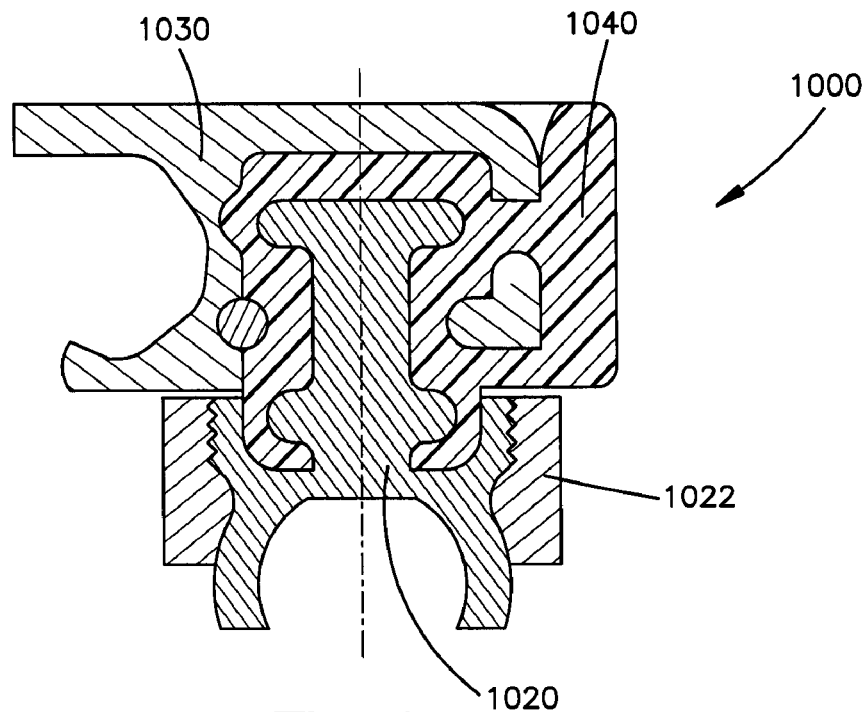
FIG. 24 shows a cross-sectional view of a dynamic pedicle screw fixation clamp according to a sixth exemplary embodiment of the present invention.

Referring to FIG. 24, the dynamic pedicle screw fixation clamp 1000 of a sixth preferred embodiment may include a pedicle screw clamping assembly 1020, a rod clamping assembly 1030 and a flexible element 1040 wherein the flexible element 1040 is located between the rod clamping assembly 1030 and the pedicle screw clamping assembly 1020. As shown, the rod clamping assembly 1030 may be in the form of a side opening rod clamping assembly. The pedicle screw clamping assembly 1020 is preferably surrounded by a locking ring 1022. The flexible element 1040 connecting the pedicle screw clamping assembly 1020 and the rod clamping assembly 1030 is preferably made of a damper material. In use, the damper material 1040 flexes, compresses and stretches to allow the pedicle screw clamping assembly 1020 to move with respect to the rod clamping assembly 1030. Although, a damper material element is described, the use of mechanical springs is also possible.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

We claims:

1. A dynamic bone fixation element for coupling a load carrier to a patient's bone or bone fragments, the dynamic bone fixation element comprising:

a bone engaging component for engaging the bone or bone fragments, the bone engaging component including an outer surface, a proximal end, a distal end, and a lumen extending at least partially from the proximal end of the bone engaging component, the lumen defining an inner surface; and a load carrier engaging component including a head portion for engaging the load carrier and a shaft portion extending from the head portion, the shaft portion having a proximal end, a distal end and an outer surface, the shaft portion being sized and configured to at least partially extend into the lumen formed in the bone engaging component, wherein at least a portion of the shaft portion has a diameter $D_S$ and at least a portion of the lumen has a diameter $D_L$, the diameter $D_L$ being greater than the diameter $D_S$ so that at least a portion of the outer surface of the shaft portion is spaced away from at least a portion of the inner surface of the lumen, the distal end of the shaft portion is coupled to the lumen at a position distally of the proximal end of the bone engaging component so that the head portion moves with respect to the bone engaging component, the bone engaging component includes a plurality of threads formed on the outer surface thereof for engaging the bone or bone fragments, the outer surface of the shaft portion is welded to the inner surface of the lumen by welding in-between adjacent threads formed on the outer surface of the bone engaging component.

2. The dynamic bone fixation element of claim 1, wherein the inner surface of the lumen is tapered at an angle θ such that the diameter $D_L$ of the lumen at a proximal end thereof is larger than the diameter $D_L$ of the lumen at a position distally of the proximal end.

3. The dynamic bone fixation element of claim 2, wherein the taper angle θ of the lumen is less than about ten degrees.

4. The dynamic bone fixation element of claim 1, wherein the shaft portion is integrally formed with the head portion.

5. The dynamic bone fixation element of claim 1, wherein the shaft portion is welded to the bone engaging component within the lumen at a position proximate to the distal end of the bone engaging component.

6. The dynamic bone fixation element of claim 1, wherein the shaft portion is coupled to the bone engaging component within the lumen with a press fit connection.

7. The dynamic bone fixation element of claim 1, wherein the distal end of the shaft portion has a diameter greater than the diameter $D_L$ of the lumen.

8. The dynamic bone fixation element of claim 1, wherein the shaft portion includes one or more textured surfaces formed thereon.

9. The dynamic bone fixation element of claim 8, wherein the textured surfaces elastically deform as the shaft portion is being inserted into the lumen and thereafter return to a larger original size so that the textured surface press against the inner surface of the lumen to increase a contact pressure between the outer surface of the shaft portion and the inner surface of the lumen.

10. The dynamic bone fixation element of claim 8, wherein the textured surface is a plurality of radially extending ridges formed on a portion of the shaft portion.

11. The dynamic bone fixation element of claim 8, wherein the textured surface is a plurality of longitudinal extending ridges formed on a portion of the shaft portion.

12. The dynamic bone fixation element of claim 8, wherein the textured surface is a plurality of radially extending ridges and a plurality of longitudinal extending ridges formed on a portion of the shaft portion.

13. The dynamic bone fixation element of claim 1, wherein the distal end of the shaft portion is welded to the inner surface of the lumen.

14. The dynamic bone fixation element of claim 1, wherein the head portion includes a driving element for engaging a tip formed on a drive tool, the head portion including a plurality of through holes for receiving a plurality of pins formed on the tip of the drive tool, the pins being sized and configured to extend through the head portion of the load carrier engaging component and into contact with the bone engaging component so that the plurality of pins contact both the load carrier engaging component and the bone engaging component such that rotation of the drive tool simultaneously rotates both the load carrier engaging component and the bone engaging component.

15. The dynamic bone fixation element of claim 1, wherein the head portion includes a driving element for engaging a tip formed on a drive tool, the head portion including one or more projections extending therefrom and the bone engaging component includes one or more recesses formed therein so that the projection extends into the recess so that rotation of the drive tool simultaneously rotates both the load carrier engaging component and the bone engaging component.

16. The dynamic bone fixation element of claim 1, wherein the bone engaging component is made from a biocompatible metal selected from the group consisting of TAV and TAN and the load carrier engaging component is made from cobalt chromium.

* * * * *